(12) United States Patent
Greer

(10) Patent No.: US 8,039,468 B2
(45) Date of Patent: Oct. 18, 2011

(54) METHOD OF INHIBITION OF RESPIRATORY DEPRESSION USING POSITIVE ALLOSTERIC AMPA RECEPTOR MODULATORS

(75) Inventor: John Greer, Edmonton (CA)

(73) Assignee: The Governors of the University of Alberta, Edmonton, AB (CA)

( * ) Notice: Subject to any disclaimer, the term of this patent is extended or adjusted under 35 U.S.C. 154(b) by 996 days.

(21) Appl. No.: 11/847,835

(22) Filed: Aug. 30, 2007

(65) Prior Publication Data

US 2008/0261962 A1    Oct. 23, 2008

Related U.S. Application Data

(60) Provisional application No. 60/824,245, filed on Aug. 31, 2006.

(51) Int. Cl.
*A61K 31/5377* (2006.01)
*A61K 31/435* (2006.01)
*A61K 31/357* (2006.01)

(52) U.S. Cl. .................. 514/231.5; 514/315; 514/453

(58) Field of Classification Search .............. 514/231.5, 514/315, 453
See application file for complete search history.

(56) References Cited

U.S. PATENT DOCUMENTS

| | | | |
|---|---|---|---|
| 6,730,677 B2 * | 5/2004 | Rogers et al. ............ | 514/254.03 |
| 6,943,159 B1 | 9/2005 | Gouliaev et al. | |
| 7,026,475 B2 | 4/2006 | Ceci et al. | |
| 2002/0055508 A1 | 5/2002 | Rogers et al. | |
| 2004/0082519 A1 | 4/2004 | Hedner et al. | |
| 2006/0276532 A1 | 12/2006 | Dominguez-Manzanares | |

FOREIGN PATENT DOCUMENTS

| | | |
|---|---|---|
| WO | WO 94/02475 A1 | 2/1994 |
| WO | WO 98/35950 A1 | 8/1998 |

OTHER PUBLICATIONS

Ge et al. (Journal of Physiology, vol. 509.1, pp. 255-266; 1998).*
Sebel et al. (British Medicla Journal, vol. 289, pp. 1581-1582; 1984).*
Looi-Lyons et al. (Journal of Clinical Anesthesia, vol. 8, pp. 151-156; 1996).*
Arai, et al. "Modulation of AMPA receptor kinetics differentially influences synaptic plasticity in the hippocampus," 2004,m *Neurosci.*, 123(4):1011-1024.
Bissonnette et al., "Non-NMDA Receptors Modulate Respiratory Drive in Fetal Sheep," 1997, Journal of Physiology, 501.2, 415-423.
Black, "Therapeutic potential of positive AMPA modulators and their relationship to AMPA receptor subunits. A review of preclinical data.," 2005, Psychopharmacol., 179, 154-163.
Denavit-Saubie et al., "Effects of opiates and methionine-enkephalin on pontine and bulbar respiratory neurones of the cat," 1978, *Brain Res.*, 155(1):55-67.
Feldman et al. "Looking for inspiration: new perspectives on respiratory rhythm,"2006, *Nat. Rev. Neurosci.*, 7(3):232-24.
Funk, G.D., et al. "Generation and transmission of respiratory oscillations in medullary slices: role of excitatory amino acids," (1993) *J. Neurophysiol.*, 70(4):1497-1515.
Funk, G.D., et al. "Modulation of neural network activity in vitro by cyclothiazide, a drug that blocks desensitization of AMPA receptors" 1995, *J. Neurosci.*, 15:4046-4056.
Goff, D.C., et al. "A placebo-controlled pilot study of the ampakine CX516 added to clozapine in schizophrenia," *J. Clin. Psychopharmacol.*, 21(5):484-487.
Greer J.J., et al. "Role of excitatory amino acids in the generation and transmission of respiratory drive in neonatal rat," 1991, *J. Physiol.*, 437:727-749.
Greer, J.J., et al. Respiratory and locomotor patterns generated in the fetal rat brain stem-spinal cord in vitro, *J. Neurophysiol.*, 67:996-999.
Horner et al., "Update in Sleep and Control of Ventilation," 2007, Am. J. Respir. Crit. Care Med. 175, 426-431.
Johnson et al. "Modulation of respiratory rhythm in vitro: role of Gi/o protein-mediated mechanisms," 1996, *J. Appl. Physiol.*, 80(6):2120-33.
Lauterborn et al. "Positive Modulation of AMPA Receptors Increases Neurotrophin," 2000, *J. Neurosci*, 20:8-21.
Lynch "Glutamate-based therapeutic approaches: ampakines," 2006, *Curr. Op. Pharmacol,.* 6:82-88.
Nagarajan et al. "Mechanism and impact of allosteric AMPA receptor modulation by the ampakine CX546," 2001, *Neuropharmacol.*, 41:650-663.
Ren et al., "Ampakines Alleviate Respiratory Depression in Rats," 2006, Am. J. Respir. Crit. Care Med., 174, 1384-1391.
Shook et al., "Differential roles of opioid receptors in respiration, respiratory disease, and opiate-induced respiratory depression." 1990, *Am. Rev. Respir. Dis.*, 142(4):895-909.
Thoby-Brisson et al. "Expression of Functional Tyrosine Kinase B Receptors by Rhythmically Active Respiratory Neurons in the Pre-Bötzinger Complex of Neonatal Mice," 2003, *J. Neurosci.*, 23:7685-7689.
Whitney et al., "AMPA Glutamate Receptors and Respiratory Control in the Developing Rat: Anatomic and Pharmacological Aspects," 2000, Am. J. Physiol. Regulatory Integrative Comp. Physiol., 278: R520-528.

\* cited by examiner

*Primary Examiner* — Jeffrey S Lundgren
*Assistant Examiner* — Nelson Blakely, III
(74) *Attorney, Agent, or Firm* — Kilpatrick Townsend & Stockton LLP

(57) ABSTRACT

The invention is directed to a method for alleviating respiratory depression in a subject as a result of disease of pharmacological agents such as opiates, opioids or barbiturates. The invention also discloses pharmaceutical compositions for use with the method, the composition containing in combination, an analgesic, anaesthetic, or a sedative and a positive allosteric AMPA receptor modulator in an amount sufficient to reduce or inhibit respiratory depression caused by the analgesic, anaesthetic, or sedative.

11 Claims, 12 Drawing Sheets

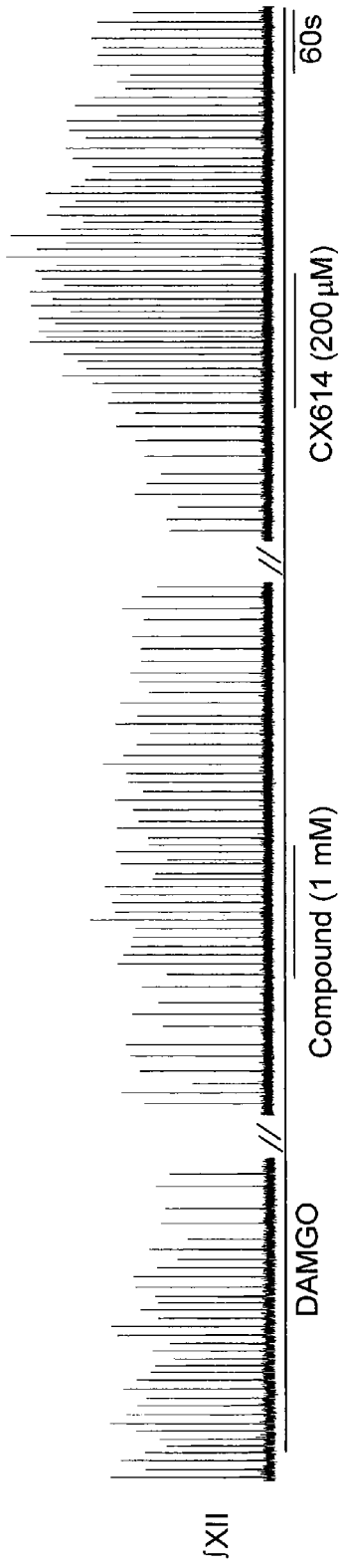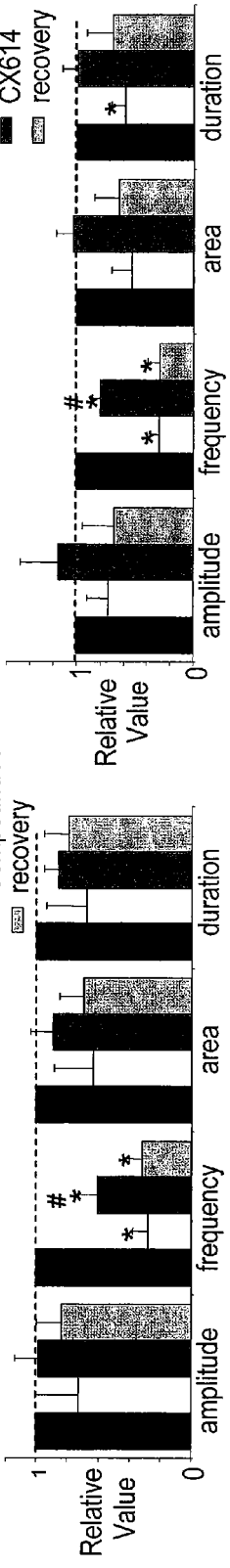
FIG. 6A
FIG. 6B

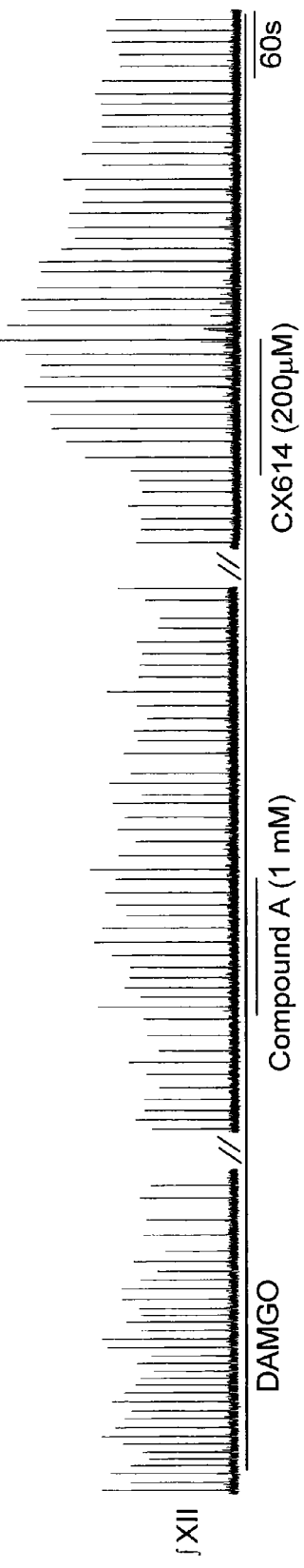
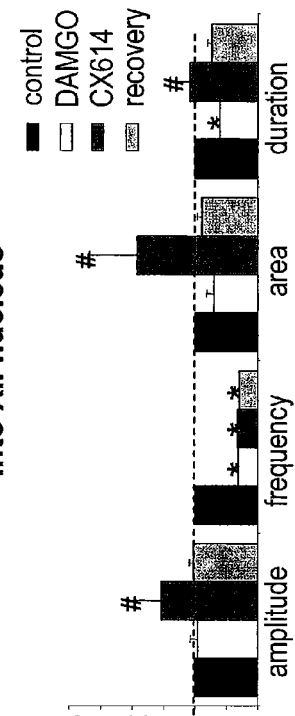
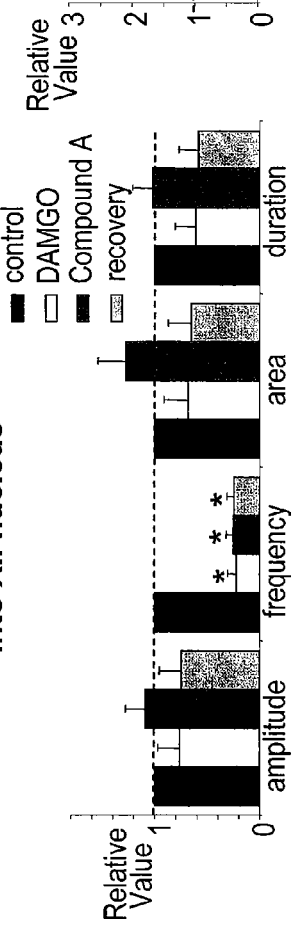
FIG. 7A
FIG. 7B

METHOD OF INHIBITION OF RESPIRATORY DEPRESSION USING POSITIVE ALLOSTERIC AMPA RECEPTOR MODULATORS

CROSS-REFERENCES TO RELATED APPLICATIONS

This application claims benefit of U.S. Provisional Application No. 60/824,245, filed Aug. 31, 2006, which is herein incorporated by reference in its entirety.

FIELD OF THE INVENTION

The invention is directed towards a method for reducing or inhibiting respiratory depression (RD) in a subject as a result of disease or pharmacological agents. Further, a method for reversing drug-induced respiratory depression without reversing analgesic or sedation response is provided. Furthermore, a method and pharmaceutical composition is provided for inducing opiate, opioid or barbiturate analgesia, anesthesia or sedation in a subject without suppressing respiration.

BACKGROUND OF THE INVENTION

There is a concerted effort by medical research toward understanding the neurochemical control of respiratory rhythm generating networks as well as the premotor and motoneuron circuits that determine activity patterns of respiratory muscles. Insights derived from experimental work are important for developing pharmacological interventions to alleviate respiratory depression in a variety of medical conditions. In this regard, a specific region within the ventrolateral medulla, the preBötzinger complex (preBötC) is a major region of investigative focus as playing a critical role in generating rhythmic inspiratory drive (reviewed in Feldman et al. (2006) *Nat. Rev. Neurosci.* 7(3):232-241).

Within the preBötC, glutamatergic synaptic signaling mediated by non-NMDA receptors (primarily α-amino-3-hydroxy-5-methyl-4-isoxazolepropionic acid (AMPA) receptors) is particularly important for maintaining respiratory rhythm. See, Greer J. J., et al. (1991) *J. Physiol.* 437:727-749; Funk, G. D., et al. (1993) *J. Neurophysiol.* 70(4):1497-1515. Block of non-NMDA receptors with the antagonist 6-cyano-7-nitroquinoxaline-2,3-dione (CNQX) causes a dose-dependent decline, and eventual cessation, of respiratory frequency and inspiratory drive to cranial and spinal motoneurons. Elevation of endogenously released glutamate levels with glutarnatergic uptake inhibitors (Funk, G. D., et al. (1993)) or reduction of AMPA receptor desensitization (see, Funk, G. D., et al. (1995) *J. Neurosci.* 15:4046-4056) leads to increases in respiratory frequency in vitro.

Opiates have long been known to disrupt respiratory rhythm and to depress breathing and respiratory sensitivity to $CO_2$ (reviewed in Shook et al., (1990) *Am. Rev. Respir. Dis.* 142(4):895-909). The pons and medulla are known to be the primary sites where opiate drugs produce these respiratory effects (Id.). Endogenous opioids as well as µ- and δ-subtypes of opioid receptors are present in essentially all respiratory regions of the pons and medulla (Yeadon and Kitchen, (1989) *Prog Neurobiol.* 33(1):1-16). In vivo and in vitro investigations have shown that exogenous opioids depress inspiratory and expiratory neuronal activity postsynaptically (Denavit-Saubie', Champagnat and Zieglgansberger, (1978) *Brain Res.* 155(1):55-67.) as well as presynaptically (Johnson, Smith and Feldman, (1996) *J. Appl. Physiol.* 80(6):2120-33). The underlying cellular mechanisms responsible for the opiate effects on respiration have not, however, been elucidated.

Opiate agents are widely used in medicine. Because they depress breathing, however, their use is contraindicated in many instances, especially in patients with compromised cardiovascular and pulmonary function. Thus, there has been a long-felt need to harness the analgesic power of the opiates and opioids, without depressing the respiratory function of the patient.

The present invention addresses this and other needs by disclosing that positive allosteric AMPA receptor modulators provide a novel pharmacological means of countering respiratory depression. The present invention demonstrates that a positive allosteric AMPA receptor modulator, which can potentiate AMPA receptor-mediated currents (Nagarajan, N., et al. (2001) *Neuropharmacol.* 41:650-663) is an effective means of countering respiratory depression.

SUMMARY OF THE INVENTION

In one aspect of the invention, a method is provided for reducing or inhibiting respiratory depression in a subject having respiratory depression, comprising administering to the subject an amount of a positive allosteric AMPA receptor modulator, the amount being sufficient to reduce or inhibit respiratory depression. In one embodiment of the invention, the subject is a mammal. In another embodiment, the subject is a human.

In some embodiments of the invention, the respiratory depression results from a drug overdose. In some embodiments, the drug is an alcohol, an opiate, an opioid, a barbiturate, an anaesthetic, or a nerve toxin. In other embodiments, the subject has respiratory depression resulting from a medical condition. Typical medical conditions can include central sleep apnea, stroke-induced central sleep apnea, obstructive sleep apnea, congenital hypoventilation syndrome, obesity hypoventilation syndrome, sudden infant death syndrome, Retts syndrome, spinal cord injury, traumatic brain injury, Cheney-Stokes respiration, Ondines curse, Prader-Willi's syndrome, and drowning.

Another aspect of the invention is a method for inducing analgesia, anaesthesia, or sedation in a subject while simultaneously reducing or inhibiting respiratory depression in the subject without altering, in a clinically meaningful way, the analgesic, anaesthetic, or sedative effect of the central respiratory depressant. The method comprises administering to the subject a therapeutically effective amount of a central respiratory depressant, sufficient to induce analgesia, anaesthesia, or sedation in a subject, and concomitantly administering a therapeutically effective amount of a positive allosteric AMPA receptor modulator sufficient to reduce or inhibit respiratory depression, without affecting, in a clinically meaningful way, the analgesic, anaesthetic, or sedative effect of the central respiratory depressant.

Another aspect of the present invention is a pharmaceutical composition for inducing analgesia, anaesthesia, or sedation in a subject, while simultaneously reducing or inhibiting respiratory depression in the subject, the pharmaceutical composition comprising a central respiratory depressant, a positive allosteric AMPA receptor modulator, and a suitable carrier.

In some embodiments, the central respiratory depressant is an alcohol, an opiate, an opioid, or a barbiturate. In some embodiments of the present invention, the opiate or opioid is selected from the group consisting of alfentanil, buprenorphine, carfentanil, codeine, dihydrocodeine, diprenorphine, etorphine, fentanyl, heroin, hydrocodone, hydromorphone, LAAM, levorphanol, meperidine, methadone, morphine, nalbuphine, naltrexone, beta-hydroxy-3-methylfentanyl, oxycodone, oxymorphone, pentazocine, propoxyphene, remifentanil, sufentanil, tilidine, tramadol, enriched or pure enantiomers or diastereomers thereof; racemic mixtures thereof; and pharmaceutically-suitable salts thereof; the barbiturate is selected from the group consisting of allobarbital, amylbarbital, butabarbital, hexabarbital, mephobarbital, methohexital, pentobarbital, phenobarbital, phenethylbarbital, secobarbital, talbutal and thiopental.

In some embodiments of the present invention, the compound is an AMPAKINE® type positive allosteric AMPA receptor modulator. In other embodiments, the positive allosteric AMPA receptor modulator is selected from the group consisting of CX546, CX614, 1-(benzofurazan-5-ylcarbonyl)-4,4-difluoropiperidine; and 4-(benzofurazan-5-ylcarbonyl)morpholine. Additional positive allosteric AMPA receptor modulator compounds suitable for use in the practice of the invention will be well known to persons of skill in the art.

BRIEF DESCRIPTION OF THE FIGURES

FIG. 1 shows that CX546 stimulates frequency of rhythmic respiratory activity generated by brainstem-spinal cord preparations.

FIG. 2 shows that CX546 stimulates frequency of rhythmic respiratory activity generated by medullary slice preparations. FIG. 2A (a) shows that when perfused with 3 mM $[K^+]_o$ bathing medium, rhythmic activity was present shortly after slice production. FIG. 2A(b) shows that burst amplitude and frequency gradually diminished and stopped in <60 min. FIG. 2A(c)-(d) show that after cessation of rhythmic activity (in 3 mM $[K^+]_o$) bath-application of CX546 restored rhythmic activity of XII motoneurons, and that the respiratory rhythm persisted for more than 3 h in the presence of CX546.

FIG. 4 shows CX546 counters opioid-induced depression of respiratory frequency and amplitude generated by perfused heart in situ preparations.

FIG. 6 shows focal injection of positive allosteric AMPA receptor modulator compounds CX614 and 4-(benzofurazan-5-ylcarbonyl)morpholine (Compound A) into the preBötC alleviates DAMGO-induced suppression of respiratory rhythm in newborn rat medullary slice preparations. FIG. 6A shows rectified and integrated suction electrode recordings of XII cranial root discharge (∫XII) from a postnatal day (P)2 medullary slice preparation. The frequency of inspiratory bursts is markedly decreased by bath-application of the μ-opiate receptor agonist Tyr-D-Ala-Gly-N-methyl-Phe-Gly-ol-enkephalin (DAMGO or DAGO). The timing of the drug application is indicated by the horizontal lines. Focal application of Compound A alleviates the frequency depression. The focal application of CX614, following the washout of Compound A, while maintaining exposure to DAMGO, shows a powerful effect on the frequency and amplitude of XII motorneuron activity. FIG. 6B shows population data (n=5 preparations).

FIG. 7 shows focal injection of positive allosteric AMPA receptor modulator compounds CX614 and 4-(benzofurazan-5-ylcarbonyl)morpholine (Compound A) into the XII motorneuron nucleus alleviates DAMGO-induced suppression of inspiratory discharge amplitude in newborn rat medullary slice preparation. FIG. 7A shows rectified and integrated suction electrode recordings of XII cranial root discharge (∫XII) from a postnatal day (P)2 medullary slice preparation. The amplitude of the inspiratory bursts is decreased by bath-application of the μ-opiate receptor agonist DAMGO. Focal application of Compound A alleviates some of the amplitude depression. The focal application of CX614, following the washout of Compound A, while maintaining exposure to DAMGO, shows a powerful effect on the frequency and amplitude of XII motorneuron activity. FIG. 7B shows population data (n=5 preparations).

FIG. 10A. Current-clamp recording of membrane potential from an inspiratory neuron within the preBötC in a medullary slice preparation bathed in low extracellular K+ to induce a weak respiratory drive. The frequency of the rhythm and the inspiratory drive potential are increased by CX546. FIG. 10B. Voltage-clamp recording of membrane current from the same neuron. CX546 caused a marked increase in the amplitude of inward inspiratory drive current. All effects were reversed upon washout of CX546.

DETAILED DESCRIPTION OF THE INVENTION

I. Definitions

Figure 1A:
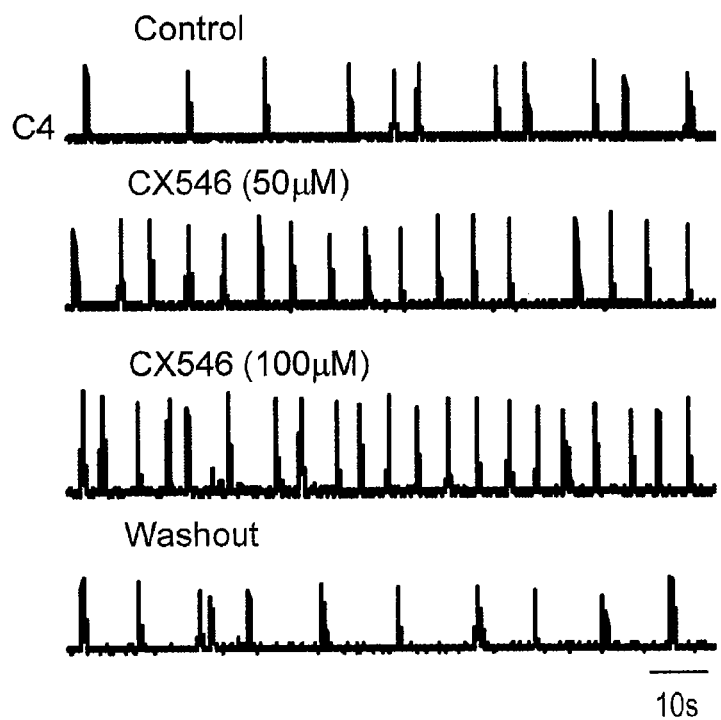
FIG. 1A denotes rectified and integrated suction electrode recordings of C4 ventral root discharge from an E20 brainstem-spinal cord preparation in response to bath application of CX546.

The phrase "respiratory depression" or "hypoventilation" as used herein refers to a variety of conditions characterized by reduced respiratory frequency and inspiratory drive to cranial and spinal motor neurons. Specifically, respiratory depression refers to conditions where the medullary neural network associated with respiratory rhythm generating activity does not respond to accumulating levels of $PCO_2$ (or decreasing levels of $PO_2$) in the blood and subsequently understimulates motoneurons controlling lung musculature.

The term "positive allosteric AMPA receptor modulator" as used herein refers to a compound that is an allosteric modulator of the AMPA-receptor complex. Positive allosteric AMPA receptor modulators enhance AMPA receptor signaling by binding to the AMPA receptor complex in its agonist-bound state to modulate the kinetics of channel closing and transmitter dissociation from the receptor and receptor desensitization. In some embodiments, the compound is an AMPA-KINE® type positive allosteric AMPA receptor modulator. Non-limiting exemplary positive allosteric AMPA receptor modulators suitable for use with the invention include 1-(1, 3-benzodioxol-5-ylcarbonyl)piperidine (1-BCP); (1-(quinoxalin-6-ylcarbonyl)piperidine (CX516); 1-(1,4-benzodioxan-6-ylcarbonyl)piperidine (CX546); 2H,3H,6aH-pyrrolidinol[2",1"-3',2']1,3-oxazino[6',5'-5,4]benzo[e]1,4-dioxan-10-one (CX614); 1-(benzofarazan-5-ylcarbonyl)-4,4-difluoropiperidine; and 4-(benzofurazan-5-ylcarbonyl)morpholine. Additional positive allosteric AMPA receptor modulators suitable for use with the invention are described herein and are known to persons of skill in the art.

The term "AMPA receptor" as used herein refers to receptors that are molecules, or complexes of molecules present in cells, particularly neurons, usually at the surface membrane, that recognize and bind to glutamate and AMPA. The binding of AMPA or glutamate to an AMPA receptor normally gives rise to a series of molecular events or reactions that result in a biological response.

The term "opiate" and "opioid" as used herein refer generically to a class of narcotic compounds characterized by having addiction-forming or addiction-sustaining properties similar to morphine or being capable of conversion into a drug having such addiction-forming or addiction-sustaining properties. Specifically, the term "opiate" denotes compounds containing the fundamental morphine or thebaine structure and possessing some affinity to any, or all, of the opioid receptor subtypes. Examples of opiates are heroin, buprenorphine, and naltrexone. An "opioid" is any compound, peptide or otherwise, which, while not containing the fundamental morphine or thebaine structure, possesses some affinity for any, or all, of the opioid receptor subtypes. Common opioids are endorphin, fentanyl and methadone. A non-exclusive list of opiates and opioids includes mophine, heroin, opium, cocaine, fentanyl, ecgonine, thebaine. Commercially-available opiates and opioids include: alfentanil, buprenorphine (SUBUTEX®), carfentanil, codeine, dihydrocodeine, diprenorphine, etorphine (IMMOBILON®), fentanyl, heroin, hydrocodone (VICODIN®), hydromorphone (DILAUDID®), LAAM, levorphanol (LEVO-DROMORAN®), meperidine (DEMEROL®), methadone (DOLOPHINE®), morphine, nalbuphine (NUBAIN®), naltrexone (TREXAN®), beta-hydroxy 3-methylfentanyl, oxycodone (PERCODAN®), oxymorphone (NUMORPHAN®), pentazocine (TALWIN®), propoxyphene (DARVON®), remifentanil (ULTIVA®), sufentanil, tilidine (VALERON®), and tramadol (ULTRAM®). The definition includes all opiates and opioids, from any source, including naturally-derived compounds, synthetic compounds, and semi-synthetic compounds. The definition also includes all isomers, stereoisomers, esters, ethers, salts, and salts of such isomers, stereoeisomers, esters, and ethers, whenever the existence of such isomers, stereoisomers, esters, and ethers is possible within the specific chemical designation.

The term "barbiturate" as used herein refers generically to a salt or ester of barbituric acid and includes any of a group of barbituric acid derivatives that act as central nervous system depressants and are used as sedatives or hypnotics. Non-limiting exemplary barbiturates include: allobarbital, amylbarbital, butabarbital, hexabarbital, mephobarbital, methohexital, pentobarbital, Phenobarbital (NEMBUTAL®), phenethylbarbital (LUMINAL®), secobarbital (SECONAL®), talbutal (LOTUSATE®), and thiopental. The definition also includes all isomers, stereoisomers, esters, ethers, salts, and salts of such isomers, steroeisomers, esters, and ethers, whenever the existence of such isomers, stereoisomers, esters, and ethers is possible within the specific chemical designation.

The term "subject" refers to a mammal, particularly a human. The term "subject" as used herein can refer to any mammal including domestic and common laboratory mammals such as non-human primates, kine, horses, pigs, goats, sheep, dogs, cats, rabbits, mice, rats, and the like.

The term "central nervous system" or "CNS" as used herein comprises the brain and the spinal cord. The term "peripheral nervous system" or "PNS" comprises all parts of the nervous system that are not part of the CNS, including the cranial and spinal nerves, and the autonomic nervous system.

As used herein the term "effective amount" or "therapeutically effective amount" refers to the amount or dosage of an agent sufficient to effectuate a desired therapeutic effect. Such amount may vary depending on the effect to be achieved and the agent used.

The terms "reducing" or "inhibiting" as used herein refers to a reduction in respiratory depression in a subject in the presence of the positive allosteric AMPA receptor modulator, as compared with the level of respiratory depression in the absence of the positive allosteric AMPA receptor modulator. The reduction in respiratory frequency and inspiratory drive is reversed or alleviated by stimulating glutamatergic synaptic signaling mediated by non-NMDA receptors (potentiation of AMPA receptor mediated currents) in the brain stem.

The phrase "concomitantly administered" as used herein refers to the administration of a first agent (e.g. an positive allosteric AMPA receptor modulator) either before, during, or after the administration of a second agent (e.g. a central respiratory depressant). The order of administration of the agents is not critical, and the administration of the two agents may completely overlap, partially overlap, or not overlap. In embodiments where the administration periods of the two agents do not overlap, the administration is still concomitant if the second agent is administered during the bioactive period of the first agent.

The term "central respiratory depressant" as used herein refers to any compound that acts on the central nervous system resulting in respiratory depression or hypoventilation. Typical central respiratory depressants can include drugs such as alcohol, benzodiazepines, barbiturates, GHB, opioids and opiates all of which can produce respiratory depression when taken in sufficient dosage. Non-limiting exemplary opiates or opioids known to act as central respiratory depressants include heroin and fentanyl.

II. Introduction

The present invention is directed to methods and compositions for reducing or inhibiting respiratory depression in a subject, by administering a positive allosteric AMPA receptor modulator to a subject in need thereof. Specifically, the invention is based in part on the surprising discovery that positive allosteric AMPA receptor modulators, such as CX546, CX614, and 4-(benzofurazan-5-ylcarbonyl)morpholine enhance respiratory drive and rhythmogenesis in the brain and thereby counteract respiratory depression.

The combined use of in vitro, in situ and in vivo rat models allowed for the analyses of various positive allosteric AMPA receptor modulators on preBötC activity and respiratory motor pools in reduced and intact preparations across multiple developmental stages. In vivo studies further demonstrated the surprising result that the administration of a positive allosteric AMPA receptor modulator not only alleviates opioid-induced respiratory depression, but does so without altering, in a clinically meaningful way, the analgesic effect of the opioid. These and other aspects of the present invention are discussed in more detail below and in the examples that follow.

A. Respiratory Depression

1. Causes for Respiratory Depression

The methods and compositions of the present invention are directed toward subjects having respiratory depression. The causes of respiratory depression that can be treated with the methods and compositions disclosed herein are varied, and include drug overdose, pharmaceutical use of central respiratory depressants, and medial conditions, including trauma.

In some embodiments, the respiratory depression results from a drug overdose. Drug classes that are known to cause respiratory depression when taken in excess include narcotics, benzodiazepines, opiates, opioids, barbiturates and alcohol. Non-limiting exemplary barbiturates that can cause respiratory depression when taken in excess include amobarbital (SODIUM AMYTAL®), aprobarbital (ALURATE®), butabarbital (BUTISOL®), butalbital (FIORINAL®), hexobarbital (SOMBULEX®), methylphenobarbital (MEBARAL®), pentobarbital (NEMBUTAL®), phenobarbital (LUMINAL®), secobarbital (SECONAL®), sodium thiopental (SODIUM PENTOTHAL®), and talbutal (LOTUSATE®). Non-limiting exemplary benzodiazepines include alprazolam (XANAX®), clonazepam (KLONOPIN®), diazepam (VALIUM®), flunitrazepam (ROHYPNOL®), lorazepam (ATIVAN®), nitrazepam (MOGADON®), and temazepam (RESTORIL®). Non-limiting exemplary non-benzodiazepine GABA-A modulators include zaleplon (SONATA®), zopiclone (LUNESTA®), and zolpidem (AMBIEN®). Non-limiting exemplary deliriants that can cause respiratory depression when taken in excess include: atropine, diphenhydramine hydrochloride (BENADRYL®), dimenhydrinate (DRAMAMINE®), and scopolamine. Non-limiting exemplary dissociative anaesthetics that can cause respiratory depression when taken in excess include: fluorathane and related volatile anaesthetics, dextromethorphan (DXM), ketamine (KETASET®), nitrous oxide, phencyclidine (PCP), salvinorin A, (found in Salvia divinorum), and Opium (Papaver somniferum). Non-limiting exemplary opioids that can cause respiratory depression when taken in excess can include: codeine, fentanyl (DURAGESIC®, ACTIQ®), heroin, hydrocodone (VICODIN®), hydromorphone (DILAUDID®), meperidine (DEMEROL®), methadone (METHADOSE®), morphine, oxycodone (OXYCONTIN®, ROXICODONE®), oxymorphone (OPANA®), and dextropropoxyphene (DARVOCET®).

In some embodiments, respiratory depression occurs in a subject having a medical condition. Non-limiting exemplary medical conditions that can cause respiratory depression include: central sleep apnea, stroke-induced central sleep apnea, obstructive sleep apnea, sleep apnea resulting from Parkinson's disease, congenital hypoventilation syndrome, sudden infant death syndrome, Retts syndrome, Cheney-Stokes respiration, Ondines curse, and Prader-Willi's syndrome. In some embodiments, the subject has respiratory depression as a result of a traumatic injury or neurodegenerative disease. Non-limiting exemplary traumatic injuries that can be associated with respiratory depression include spinal cord injury, traumatic brain injury, and drowning. Non-limiting exemplary neurodegenerative diseases include Parkinson's disease, spinal muscular atrophy, amyotrophic lateral sclerosis, Huntington's disease and stroke.

2. Recognizing Respiratory Depression in a Subject

Exemplary causes of respiratory depression that can be treated using the methods and compositions as disclosed herein are described above. In some embodiments, a person of ordinary skill in the art will be able to recognize a subject having respiratory depression by direct observation. Symptoms of respiratory depression can include hypopnea, which is characterized by a slow or shallow respiratory rate. Clinically significant hypopnea is characterized by a 50% or greater reduction in air flow and is associated with a 3% or greater desaturation in blood $O_2$ levels for 10 seconds or longer. In some embodiments, a subject having respiratory depression will show signs of cyanosis, which is a bluish coloration of the skin due to the presence of deoxygenated hemoglobin in blood vessels near the skin surface. Cyanosis occurs when the oxygen saturation of arterial blood falls below 85%.

In other embodiments, respiratory depression can be diagnosed using a polysomnogram. This is typically done with subjects suspected of having some form of sleep apnea or another medical condition where respiratory rhythm is disturbed during sleep. In other embodiments, respiratory acidosis (a $PaCO_2 > 6.3$ kPa or 47 mm Hg and a pH of 7.35) is indicative of respiratory depression. In yet other embodiments, respiratory depression can be routinely monitored using pulse oximetry. Respiratory airflow can be monitored with a nasal cannula connected to a pressure transducer, and thoracic and abdominal respiratory movements are routinely monitored with piezoelectric strain gauges, particularly in newborn infants.

Using the characteristic observations and tests as described above, a person of ordinary skill in the art will be able to recognize a subject having respiratory depression, and thereby in need of treatment with a positive allosteric AMPA receptor modulator to reduce or inhibit the respiratory depression. In addition, to the observations and tests set forth above, a person of ordinary skill in the art will be aware of other characteristic signs, symptoms and tests to recognize and diagnose respiratory depression suitable for use with the present invention. The next step in the practice of the invention is administering a positive allosteric AMPA receptor modulator (as described in more detail below) to a subject having respiratory depression as described above.

B. Positive Allosteric AMPA Receptor Modulators

1. Specificity of Positive Allosteric AMPA Receptor Modulator Action on Respiratory Networks Positive allosteric AMPA receptor modulators are compounds that act allosterically to positively modulate AMPA receptor currents. Positive allosteric AMPA receptor modulators do not act by directly stimulating neural activation, but rather by "upmodulating" (allosteric modulation) neural activation and transmission in neurons that contain AMPA-type glutamate receptors. Positive allosteric AMPA receptor modulators bind to the AMPA-receptor at a site other than the glutamate binding site, but the binding itself does not give rise to ion-fluxes through the receptor. However, when a glutamate molecule binds to an AMPA-receptor that has an positive allosteric AMPA receptor modulator bound to it the subsequent ion flux is of longer duration that it would have been in the absence of the positive allosteric AMPA receptor modulator being bound to the receptor. Thus, in the presence of a positive allosteric AMPA receptor modulators, post-synaptic neurons are activated by much lower concentrations of glutamate than post-synaptic neurons that are not bound by a positive allosteric AMPA receptor modulators.

The finding that the positive allosteric AMPA receptor modulators, such as CX546, CX614 and 4-(benzofurazan-5-ylcarbonyl)morpholine, stimulated breathing without widespread activation of neuronal circuits as detailed in the examples is surprising given the ubiquitous distribution of AMPA receptors within the central nervous system. Even more surprising is the discovery that positive allosteric AMPA receptor modulators alleviate respiratory depression in light of studies showing that positive allosteric AMPA receptor modulators (e.g. AMPAKINE® type positive allosteric AMPA receptor modulators) chronically elevate the production of BDNF in hippocampal and cortical neurons (see, Lauterborn, J. C. et al. (2000) *J. Neurosci* 20:8-21) because BDNF decreases, rather than increases, the frequency of respiratory rhythm in medullary slice preparations (see, Thoby-Brisson, M., et al. (2003) *J. Neurosci.* 23:7685-7689).

2. Positive Allosteric AMPA Receptor Modulator Compounds

The invention is based in part on the surprising discovery that administration of an effective amount of a positive allosteric AMPA receptor modulator compound can reduce or alleviate respiratory depression in a subject in need thereof. Positive allosteric AMPA receptor modulators are a large class of structurally diverse compounds that share common functional characteristics. Specifically, positive allosteric AMPA receptor modulators are allosteric modulators of the AMPA-receptor. Positive allosteric AMPA receptor modulators do not act by directly stimulating neural activation, but rather by "upmodulating" (allosteric modulation) neural activation and transmission in neurons that contain AMPA-type glutamate receptors. Positive allosteric AMPA receptor modulators bind to the AMPA-receptor at a site other than the glutamate binding site, but the binding itself does not give rise to ion-fluxes through the receptor. However, when a glutamate molecule binds to an AMPA-receptor that has a positive allosteric AMPA receptor modulator bound to it the subsequent ion flux is of longer duration that it would have been in the absence of the positive allosteric AMPA receptor modulator being bound to the receptor. Thus, in the presence of a positive allosteric AMPA receptor modulator, post-synaptic neurons are activated by much lower concentrations of glutamate that post-synaptic neurons that are not bound by a positive allosteric AMPA receptor modulator. This can be determined using standard electrophysiology methods, as known to persons of skill in the art, and as exemplified below in the screening methods to identify positive allosteric AMPA receptor modulator compounds.

Positive allosteric AMPA receptor modulator compounds modulate the AMPA (α-amino-3-hydroxy-5-methyl-isoxazole-4-propionic acid) receptor complex by increasing the duration of glutamate-induced AMPA receptor-gated inward currents. See, Arai, A. C., et al. (2004) *Neurosci.* 123(4): 1011-1024. Positive allosteric AMPA receptor modulator compounds act by modulating the kinetics of AMPA receptor deactivation (channel closing and transmitter dissociation) and desensitization. See, Nagarajan, N., et al. (2001) *Neuropharmacol.* 41:650-663. Positive allosteric AMPA receptor modulators readily cross the blood-brain barrier and appear to be well tolerated. See, Lynch, G. (2006) *Curr. Op. Pharmacol.* 6:82-88; Goff, D. C., et al. (2001) *J. Clin. Psychopharmacol.* 21(5):484-487; Porrino, L. J., et al. (2005) *PLoS Biol.* 3(9):1639-1652.

Exemplary positive allosteric AMPA receptor modulators suitable for use in the practice of the present invention are disclosed in PCT Int'l Pub. No. WO 94/02475 and in related U.S. Pat. Nos. 5,773,434; 5,488,049; 5,650,409; 5,736,543; 5,747,492; 5,773,434; 5,891,876; 6,030,968; 6,274,600; 6,329,368; 6,943,159; 7,026,475; and U.S. Pat. Pub. No. 20020055508. Further non-limiting exemplary positive allosteric AMPA receptor modulators suitable for use with the present invention include: sulfonamide derivatives as disclosed in U.S. Pat. Nos. 6,174,922; 6,303,816; 6,358,981; 6,362,230; 6,500,865; 6,515,026; 6,552,086; PCT Int'l Pub. Nos. WO 0190057, WO 0190056, WO 0168592, WO 0196289, WO 02098846, WO 0006157, WO 9833496, WO 0006083, WO 0006148, WO 0006149, WO 9943285, WO 9833496; (bis)sulfonamide derivatives as disclosed in WO 0194306; N-substituted sulfonamide derivatives as disclosed in U.S. Pat. No. 6,525,099 and PCT Int'l Pub. No. WO 0006537; heterocyclic sulfonamide derivatives as disclosed in U.S. Pat. No. 6,355,655 and PCT Int'l Pub. Nos. WO0214294, WO0214275, and WO0006159; heterocyclyl sulfonamide derivatives as disclosed in U.S. Pat. No. 6,358,982 and PCT Int'l Pub. No. WO0006158; alkenyl sulfonamide derivatives as disclosed in U.S. Pat. No. 6,387,954 and PCT Int'l Pub. No. WO0006539; cycloalkenyl sulfonamide derivatives as disclosed in PCT Int'l Pub. No. WO2098847; cyclopentyl sulfonamide derivatives as disclosed in U.S. Pat. No. 6,639,107 and PCT Int'l Pub. No. WO0142203; cycloalkylfluoro sulfonamide derivatives as disclosed in PCT Int'l Pub. No. WO232858; acetylenic sulfonamide derivatives as disclosed in PCT Int'l Pub. No. WO0218329; 2-propane-sulfonamide compounds and derivatives as disclosed in U.S. Pat. No. 6,596,716 and PCT Int'l Pub. Nos: WO2006087169, WO2006015827, WO2006015828, WO2006015829, WO2007090840, and WO2007090841; and 2-aminobenzenesulfonamide derivatives as disclosed in WO02089734. Benzoyl piperidine, benzoyl derivatives, and pyrrolidine compounds and related structures as disclosed in U.S. Pat. Nos. 5,650,409; 5,747,492; 5,783,587; 5,852,008; and 6,274,600. Compounds based on benzoxazine ring systems as disclosed in U.S. Pat. Nos. 5,736,543; 5,962,447; 5,985,871; and PCT Int'l Pub. Nos. WO 9736907 and WO9933469; acylbenzoxazines as disclosed in U.S. Pat. No. 6,124,278, and PCT Int'l Pub. No. WO 9951240; carbonylbenzoxazine compounds as disclosed in PCT Int'l Pub. No. WO03045315; substituted 2,3-benzodiazepin-4-ones as disclosed in U.S. Pat. No. 5,891,871; benzofurazan compounds as disclosed in U.S. Pat. Nos. 6,110,935; 6,313,115; and PCT Int'l Pub. No. WO9835950. Particularly preferred benzofurazan compounds suitable for use with the invention are 1-(benzofurazan-5-ylcarbonyl)-4,4-difluoropiperidine ; 4-(benzofurazan-5-ylcarbonyl)morpholine; and the like. Benzothiazide derivatives as disclosed in PCT Int'l Pub. No. WO 9812185; and substituted 5-oxo-5,6,7,8-tetrahydro-4H-1-benzopyrans and benzothiopyrans and related compounds as disclosed in PCT Int'l Pub. No. WO0075123 are suitable for use as positive allosteric AMPA receptor modulators in the practice of the invention. Additional positive allosteric AMPA receptor modulators suitable for use with the practice of the invention are amidophosphate derivatives as disclosed in U.S. Pat. No. 6,521,605, and PCT Int'l Pub. No. WO0006176; monofluoralkyl derivatives as disclosed in PCT Int'l Pub. No. WO 0066546; and substituted quinazolines and analogs thereof as disclosed in PCT Int'l Pub. No. WO 9944612 and quainoxaline compounds and derivatives as disclosed in PCT Int'l Pub. No. WO2007060144. Additional compounds suitable for use as positive allosteric AMPA receptor modulators with practice of the invention include 2-ethoxy-4'-[3-(propane-2-sulfonylamino)-thiophen-2-yl]-biphenyl-4-carboxylic acid and derivatives thereof as disclosed in U.S. Pat. Pub. No. 20060276532; pyrrole and pyrazole compounds and derivatives thereof as disclosed in U.S. Pat. Pub. No. 20070066573; and the thiadiazine compounds and derivatives as disclosed in U.S. Pat. Pub. No. 20070004709; and the benzoxazepine compounds and derivatives as disclosed in U.S. Pat. Pub. No. 20040171605. Other compounds suitable for use as positive allosteric AMPA receptor modulators are disclosed in PCT Int'l Pub. Nos. WO 9942456, WO 0006156, WO 0157045, and U.S. Pat. No. 6,617,351.

Each of the compounds classes disclosed in the above references are suitable for use with the present invention as positive allosteric AMPA receptor modulators. A person of ordinary skill in the art will readily recognize that the compounds described above, while being structurally diverse, share the common functional characteristics of positive allosteric AMPA receptor modulators as described above and that because of these common functional characteristics, the compounds are suitable for use in the practice of the invention.

C. Screening Methods to Identify Positive Allosteric AMPA Receptor Modulators Suitable for Use in the Invention.

Compounds suitable for use with the invention are those that amplify or positively modulate the activity of the natural stimulators of AMPA receptors, particularly by amplifying the excitatory synaptic response. As disclosed above, a wide variety of structurally diverse compounds are useful with the practice of the invention and the identification of additional compounds suitable for use with the invention is routine based on the common functional characteristics shared by positive allosteric AMPA receptor modulators. Screening methods to identify additional compounds suitable for use with the invention involve a variety of accepted tests to determine whether or not the candidate compound is a positive allosteric modulator of the AMPA receptor. The primary assay is measurement of glutamate or AMPA-induced currents using whole-cell patch clamping, excised patch clamping, and enlargement of the excitatory post-synaptic potential (EPSP) in vitro brain slices such as rat hippocampal slices, or in the rat hippocampus in vivo.

The wave form of a normal EPSP is composed of: an AMPA component, which has a relatively rapid rise in time in the depolarizing direction (~5-10 msec) and which decays within ~20 msec.; an NMDA component characterized by a slow (~30-40 msec. rise time and a slow ~40-70 msec. decay time); and a GABA component in the opposite (hyperpolarizing) direction exhibiting a time course with a rise time of ~10-20 msec and a very slow decay of at least ~50-100 msec. It should be noted that the NMDA portion of the EPSP typically does not appear in normal CSF media, but can appear in low magnesium media.

The different components of the EPSP can be separately measured to assay the effect of a candidate molecule as an AMPA-receptor enhancing agent. This is specifically accomplished by adding agents that block the unwanted components, so that the detectable responses are essentially only AMPA responses. For example, an NMDA receptor blocker (e.g., AP-5, or other NMDA blockers well known in the art) and or a GABA blocker (e.g., picrotoxin or other GABA blockers well known in the art) are added to the slice preparation. To prevent epileptiform activity in the GABA-blocked slices, known agents such as tetrodotoxin can be used.

In some embodiments, an excised membrane patch assay is used for validating candidate compounds as positive allosteric AMPA receptor modulators suitable for use with the present invention involves the use of excised membrane patches, as described in Arai, et al. (1994) *Brain Res.* 638: 343-346. Specifically, outside-out patches can be obtained from pyramidal hippocampal neurons and transferred to a recording chamber. Glutamate pulses are applied and data collected with a patch clamp amplifier and digitized as described in Arai et al. (1994). Because these neurons only contain glutamatergic receptors, GABAergic currents will not be seen. NMDA currents can be blocked as described above using agents such as AP-5.

In other embodiments, potential positive allosteric AMPA receptor modulating compounds are validated using an in vitro brain slice assay. Specifically, brain slices (such as hippocampal slices) from a mammal such as a rat are prepared and maintained in an interface chamber using conventional methods known to persons of ordinary skill in the art. In embodiments where a hippocampal slice is used, EPSPs are recorded from the stratum radiatum region of CA1b and elicited from the slice by single stimulation pulses delivered once per 20 seconds to a bipolar electrode positioned in the Schaffer-commissural projections as described previously. See, Granger et al. (1993) *Synapse*, 15:326-329; Staubli, V., et al. (1994) *Proc. Nat. Acad. Sci. USA* 91:777-781; Staubli, V., et al. (1994) *Proc. Nat. Acad. Sci. USA* 91:11158-11162; and Arai, et al. (1994) *Brain Res.* 638:343-346.

In still other embodiments, the physiological effects of potential positive allosteric AMPA receptor modulator compound can be tested in vivo in anaesthetized animals according to the following procedures. Animals are maintained under anaesthesia by phenobarbitol administered using a Hamilton syringe pump. Stimulating and recording electrodes are inserted into the perforant path and dentate gyrus of the hippocampus, respectively. Once electrodes are implanted, a stable baseline of evoked responses is elicited using single monophasic pulses (100 μsec pulse duration) delivered at a rate of 3/min to the stimulating electrode. Field EPSPs are monitored until a stable baseline is achieved (about 20-30 minutes), after which a solution of test compound in HPCD is injected intraperitoneally and evoked field potentials are recorded. Evoked potentials are recorded for approximately 2 hours following drug administration or until the amplitude of the field EPSP returns to baseline. In the latter instance, it is common that an i.v. administration is also carried out with an appropriate dose of the same test compound.

Positive allosteric AMPA receptor modulators useful in the invention are those substances that cause an increased ion flux through the AMPA receptor complex channels in response to glutamatergic stimulation. Increased ion flux is typically measured as one or more of the following parameters: at least a 10% increase in decay time, amplitude of the waveform and/or the area under the curve of the waveform and or a decrease of at least 10% in rise time of the waveform, for example in preparations treated to block NMDA and GABA components. The increase or decrease is preferably at least 25-50%; most preferably it is at least 100%. How the increased ion flux is accomplished (e.g., increased amplitude or increased decay time) is of secondary importance; positive modulation is reflective of increased ion fluxes through the AMPA channels, regardless of how achieved.

III. Pharmaceutical Forms

In some embodiments, the present invention provides methods for the use of a pharmaceutical composition suitable for administering an effective amount of at least one positive allosteric AMPA receptor modulator in unit dosage form to treat a subject with respiratory depression. In still other embodiments, the composition can comprise an analgesic, an anaesthetic, or a sedative in addition to at least one positive allosteric AMPA receptor modulator in an amount sufficient to reduce or alleviate respiratory depression resulting from the analgesic, anaesthetic, or sedative. In other embodiments, the composition further comprises a pharmaceutical carrier.

Another aspect of the invention provides pharmaceutical compositions for inducing analgesia or anesthesia while simultaneously minimizing respiratory suppression, the composition comprising an opiate or opioid compound (including pharmaceutically-acceptable salts thereof) or a barbiturate (including pharmaceutically-acceptable salts thereof), admixed with a positive allosteric AMPA receptor modulator, in combination with an acceptable carrier and optionally in combination with other therapeutically-active ingredients or inactive accessory ingredients. The carrier must be pharmaceutically acceptable in the sense of being compatible with the other ingredients of the formulation and not deleterious to the recipient. The pharmaceutical compositions include those suitable for oral, sublingual, topical, transdermal, inhalation, rectal or parenteral (including subcutaneous, intramuscular and intravenous) administration.

In some embodiments the therapeutically effective components of the pharmaceutical compositions are capable of forming both pharmaceutically acceptable acid addition and/ or base salts. All of these forms are within the scope of the present invention and can be administered to a subject to treat respiratory depression.

Pharmaceutically acceptable acid addition salts of the present invention include, but are not limited to, salts derived form non-toxic inorganic acids such as hydrochloric, nitric, phosphoric, sulphuric, hydrobromic, hydriodic, hydrofluoric, phosphorous, and the like, as well as salts derived from non-toxic organic acids such as aliphatic mono- and dicarboxylic acids, phenyl-substituted alkanoic acids, hydroxy alkanoic acids, alkanedioic acids, aromatic acids, aliphatic and aromatic sulfonic acids, and the like. Non-limiting exemplary salts include sulphate, pyrosulfate, bisulfate, sulfite, bissulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, malcate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Slats of amino acids, such as arginate, gluconate, glacturonate and n-methyl glucamine are also contemplated.

Acid addition salts of the basic compounds are prepared by contacting the free base form with a sufficient amount of desired acid to produce the salt in a convention manner. The free base form can be regenerated by contacting the salt form with a base and isolating the free base in a conventional manner. The free base form differs from the salt form in certain physical properties, but are otherwise equivalent to the salt form for purposes of the present invention.

Pharmaceutically acceptable base addition salts are formed with metals or amides, such as alkali or alkaline earth metals or organic amines. Non-limiting exemplary metals that can be used include sodium, potassium, magnesium, calcium and the like. Non-limiting exemplary amines include N2, N'-dibenzylethylenediamine, chloroprocaine, choline, diethanolamine, dicyclohexamine, ethylenediamine, N-methylglucamine, and procaine.

Base addition salts of the acidic compounds are prepared by contacting the free acid form with a sufficient amount of the desired base to produce the salt in a conventional manner. The free acid form can be regenerated by contacting the salt form with an acid and isolating the free acid in a conventional manner. The free acid differs from the salt form in certain physical characteristics, but are otherwise equivalent for purposes of the invention.

Some compounds suitable for use with the present invention can exist in unsolvated and solvated forms. The solvated forms, including hydrated forms are equivalent to the unsolvated forms and are intended to be encompassed within the scope of the present invention. Certain compounds suitable for use with the present invention possess one or more chiral centers and each center can exist in a different configuration. Some of these compounds, can therefore form stereoisomers, and the present invention contemplates the use of both the individual isolated isomers and mixtures thereof.

Pharmaceutical compositions for use with the present invention can be prepared in a pharmaceutical carrier. Pharmaceutically acceptable carriers can be in any suitable form (e.g., solids, liquids, aerosols, gels, etc.). Non-limiting exemplary solid form preparations include powders, tablets, pills, capsules, cachets, suppositories, and dispersible granules. A solid carrier can be one or more substances which may also act as diluents, flavouring agents, binders, preservatives, tablet disintegrating agents, or an encapsulating material.

For injections, the agents used in the invention can be formulated in aqueous solutions, preferably in physiologically compatible buffers such as Hank's solution, Ringers solution, or physiologically buffered saline (PBS). For transmucosal or transdermal administration, penetrants appropriate to the barrier to be permeated are used in the formulation. Suitable penetrants will be known to persons of ordinary skill in the art.

In embodiments where the agents are present in powdered form, the carrier is a finely divided solid which is in a mixture with the finely divided active component. In tablets, the active agent is mixed with the carrier having necessary binding properties in suitable proportions, and pressed into the desired size and shape.

Powders and tablets typically contain from about 5% to about 70% active compound. Non-limiting exemplary suitable carriers include magnesium carbonate, magnesium stearate, talc, sugar, lactose, pectin, dextrin, starch, gelatin, tragacanth, methylcellulose, sodium carboxymethylcellulose. For suppositories, low melting wax, cocoa, butter, mixtures of fatty acid glycerides and the like can be used.

Non-limiting exemplary liquid form preparations include solutions, suspensions, and emulsions (e.g. water or water propylene glycol solutions). For parenteral injection, liquid preparations can be formulated as solutions in aqueous polyethylene glycol. For oral administration aqueous solutions can be prepared by dissolving the active components in water and adding suitable colorants, flavors, stabilizing, thickening, and suspending agents as desired.

Also contemplated are solid form preparations that are intended to be converted shortly before use to liquid preparations for oral administration. Such liquids forms include solutions, suspensions, and emulsions. Such preparations may contain in addition to the active component, colorants, flavors, stabilizers, buffers, dispersants, thickeners, solubilizing agents, and the like.

The pharmaceutical preparations is typically in unit dosage form. As such, the pharmaceutical preparation is subdivided into unit doses containing appropriate quantities of the active component(s). The unit dosage form can be a packaged preparation, the package containing discrete quantities of preparation, such as tablets, capsules, powders, or liquids in vials or ampules.

General procedures for preparing pharmaceutical preparations are well known to persons of ordinary skill in the art, and are described in, for example, Remington's Pharmaceutical Sciences, E.W. Martin ed., Mack Publishing Co. PA (1990).

A. Dosages and Routes of Administration

The present invention contemplates a variety of techniques and routes of administration of the compounds used in the practice of the invention. Non-limiting exemplary routes of administration suitable for use with the present invention include oral, sublingual, rectal, transdermal, vaginal, transmucosal, or enteric. Parenteral delivery, including intramuscular, subcutaneous, intramedullary, intrathecal, intravenous, intraarterial, intraperitoneal, intranasal, intraocular, as well as direct intraventricular injections among others are contemplated. Indeed, it is not intended that the present invention be limited to any particular route of administration.

In one aspect of the invention, the amount of positive allosteric AMPA receptor modulator administered to a subject is that of an effective amount to reduce or alleviate respiratory depression in the subject. The quantity of a positive allosteric AMPA receptor modulator in a unit dose preparation can be from about 0.001 mg/kg body weight to about 100 mg/kg body weight. Preferably the amount of a positive allosteric AMPA receptor modulator per unit dose will range from about 0.01 mg/kg to about 50 mg/kg. More preferably, the unit dose of a positive allosteric AMPA receptor modulator will be in the range of about 0.1 mg/kg to about 10 mg/kg body weight. The composition can, if desired, also contain other compatible therapeutic agents.

The exact dose to be administered to a subject having respiratory distress will depend on a number of factors unique to the individual subject to be treated, and the particular positive allosteric AMPA receptor modulator being administered, and are ultimately the responsibility of the treating physician (or veterinarian). It is contemplated that as part of the subject evaluation, it is well within the skill of the care provider to know how to and when to terminate, interrupt, or adjust administration due to toxicity, etc. Conversely, the care provider will also know how to adjust treatment to higher levels in circumstances where clinical response is inadequate, while precluding toxicity. The magnitude of an administered dose in the management of respiratory depression will vary with the particular agents administered, route of administration, the severity of the respiratory depression and the individual subjects physiology, biochemistry, etc. The severity of the respiratory depression can be evaluated in part by standard methodologies, and the dose, and frequency of administration will also depend in part on the age, body weight, sex, and response for each individual subject.

All patents, patent applications, and other publications cited in this application are hereby incorporated by reference in their entirety.

IV. Examples

The following examples are included for illustration purposes and are not intended to be construed as a limitation on the invention in any way. It will be appreciated by those of skill in the art that the techniques disclosed herein and in the examples that follow represent techniques discovered by the inventor to function well in the practice of the invention, and can thus be considered to represent preferred modes for practice of the invention. However, those skilled in the art will also recognize, in light of the present disclosure, that many changes can be made to the specific embodiments disclosed herein and obtain similar results without departing from the spirit or scope of the invention.

Example 1

Models for Studying Positive Allosteric AMPA Receptor Modulator Activity in Vitro This example details effects of positive allosteric AMPA receptor modulators on patterns of respiratory related activity using various in vitro models under controlled conditions. Specifically, these experiments demonstrated that positive allosteric AMPA receptor modulators (e.g. CX546, CX614, and 4-(benzofurazan-5-ylcarbonyl)morpholine) markedly enhanced the frequency of respiratory rhythm in vitro in E18-P0 rats, and restored depressed rhythm in older neonates in both the brainstem-spinal cord and medullary slice preparations.

A. Brainstem-Spinal Cord Preparation

The fetal and neonatal brainstem-spinal cord preparations have been well-characterized and shown to generate complex, coordinated patterns of respiratory-related activity. See, Smith J. C. et al. (1990) and Greer, J. J. et al. (1992). Recordings from cervical ventral and hypoglossal cranial roots provide information regarding the pharmacology of respiratory rhythm generating networks and the pathways transmitting that respiratory drive to key output components of the respiratory motor system, without the confounding influence of peripheral chemoreceptors and supramedullary structures.

Brainstem-spinal cord preparations were carried out as follows: Sprague-Dawley (SD) rat fetuses were delivered from timed-pregnant dams anesthetized with halothane (2% delivered in 95% $O_2$ and 5% $CO_2$) and maintained at 37° C. by radiant heat, following procedures approved by the Animal Welfare Committee at the University of Alberta. The timing of pregnancies was determined by vaginal lavage of the dam. Newborn rat pups were anesthetized with metofane. Newborn pups and embryos were then decerebrated and the brainstem-spinal cord was dissected following procedures similar to those established for perinatal rats. See, Smith, J. C., et al. (1990) *J. Neurophysiol.* 64:1149-1169; Greer, J. J., et al. (1992) *J. Neurophysiol.* 67:996-999. The neuraxis was continuously perfused at 27±1° C. (perfusion rate 5 ml/minute, chamber volume of 1.5 ml) with modified Kreb's solution that contained (mM): 128 NaCl, 3.0 KCl, 1.5 $CaCl_2$, 1.0 $MgSO_4$, 24 $NaHCO_3$, 0.5 $NaH_2PO_4$, and 30 D-glucose equilibrated with 95% $O_2$-5% $CO_2$ (pH=7.4).

Figure 1B:
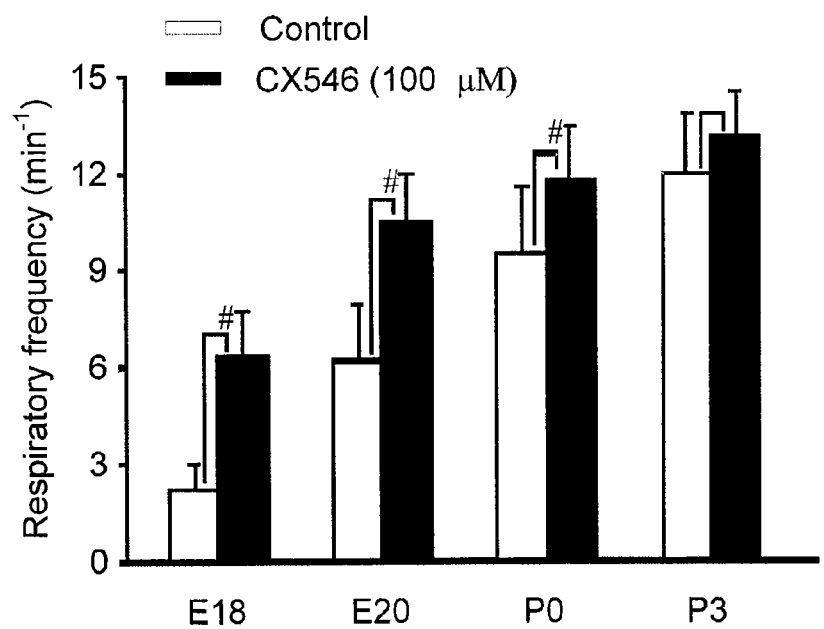
FIG. 1B denotes population data showing changes in respiratory frequency of brainstem-spinal cord preparations in response to bath application of CX546 at different perinatal ages (n=4-5 for each age; # indicates significant difference between control and CX546; $p<0.05$).

FIG. 1A shows a representative example of the respiratory discharge produced by an embryonic day (E)20 brainstem-spinal cord preparation. The frequency of rhythmic respiratory discharge was markedly enhanced by the addition of CX546 (50-100 μM) to the bathing medium. Population data showing the increase in respiratory frequency compared to control for ages E18-P3 are provided in FIG. 1B. In perinatal preparations (E18-P0), that often have a slower baseline rhythm compared to older neonates (see, Greer, J. J. et al. (1992)), CX546 caused a significant increase in frequency. By P3, however, CX546 had no effect on the baseline frequency of the more robust respiratory output generated by these older brainstem-spinal cord preparations.

B. Medullary Slice Preparations

The medullary slice preparation is a derivative of the brainstem-spinal cord preparation. See, Smith J. C., et al. (1991). It contains the minimum component of neuronal populations within the ventrolateral medulla necessary for generating a respiratory rhythm, the preBötC. The medullary slice also contains a significant portion of the rostral ventral respiratory group, hypoglossal nucleus and XII cranial nerve rootlets from which inspiratory motor discharge is recorded.

Brainstem-spinal cords isolated from newborn rats were pinned down, ventral surface upward, on a paraffin-coated block. See, Funk, G. D., et al. (1993); Smith, J. C., et al. (1991). The block was mounted in the vise of a vibratome bath (Leica, VT1000S). The brainstem was sectioned serially in the transverse plane starting from the rostral medulla to within approximately 150 μm of the rostral boundary of the preBötC, as judged by the appearance of the inferior olive. A single transverse slice containing the preBötC and more caudal reticular formation regions was then cut (500-600 μm thick), transferred to a recording chamber and pinned down onto a Sylgard elastomer. The medullary slice was continuously perfused with a bathing solution identical to that used for the brainstem-spinal cord preparation with the exception that in some cases the $K^+$ concentration was increased to 9 mM which facilitates long-term generation of stable rhythm (>5 hours) by these preparations. See, Funk, G. D., et al. (1993); Smith, J. C., et al. (1991). Recordings were made from the hypoglossal (XII) cranial nerve roots, cervical (C4) ventral roots and neuronal population discharge within the ventrolateral medulla with suction electrodes placed over the nerve roots or on the surface of the rhythmic slice preparations.

Figure 2A:
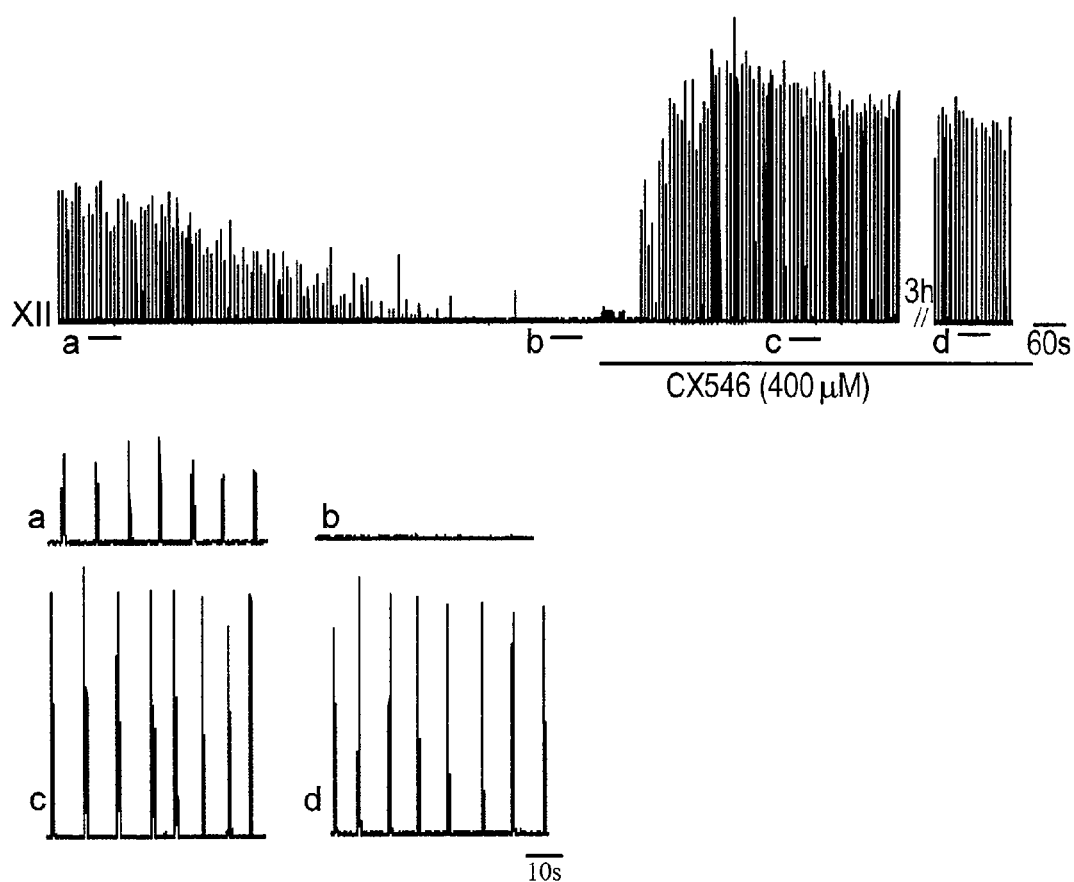
FIG. 2A denotes long-term recording (>3 hours) from a P2 medullary slice preparation perfused with bathing medium containing 3 mM $[K^+]_o$, showing rectified and integrated hypoglossal nerve root (XII) activity. The bottom traces in FIG. 2A (a-d) show expanded records of respiratory discharge at specific periods during the recording.
Figure 2B:
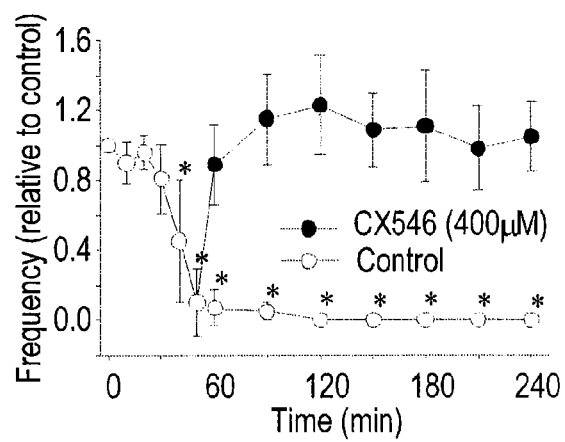
FIG. 2B denotes population data showing time course of changes in respiratory frequency of P2 medullary slice preparations in 3 mM $[K^+]_o$ medium or 3 mM $[K^+]_o$ followed by addition of CX546 at t=60 min (n=3 for each data point post-45 minutes, n=60-45 minutes).

FIG. 2 illustrates the effects of CX546 on the respiratory rhythm generated by medullary slice preparations. The respiratory-related output generated by these slices typically shows a gradual decrease in frequency and burst amplitude and stops within approximately 60 min. when medullary slices are prepared and bathed in solution containing 3 mM [$K^+$]. Bath application. of CX546 (400 µM) to the slices after rhythmic activity ceased in 3 mM [$K^+$] caused a rapid and potent stimulation of respiratory networks. Within 2 minutes of CX546 application, frequency and amplitude were restored to 3 mM [$K^+$] bath levels, and in some cases to levels greater than that observed at any point in bathing media containing 3 mM [$K^+$]$_o$.

Figure 3A:
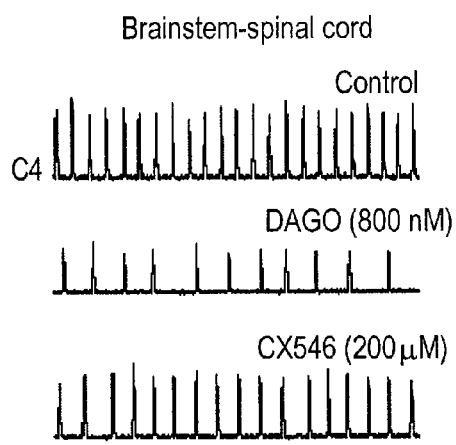
FIG. 3A denotes rectified and integrated recordings of C4 ventral roots (brainstem-spinal cord of a P1 rat) and FIG. 3B denotes rectified and integrated recordings of XII nerve roots (medullary slice of a P1 rat perfused with 9 mM $[K^+]_o$ bathing medium) in response to bath application of the μ-opioid receptor agonist Tyr-D-Ala-Gly-N-methyl-Phe-Gly-ol-enkephalin (DAGO or DAMGO). The DAGO-induced suppression of respiratory frequency and amplitude in these preparations was partially reversed by the subsequent bath-application of CX546.
Figure 3B:
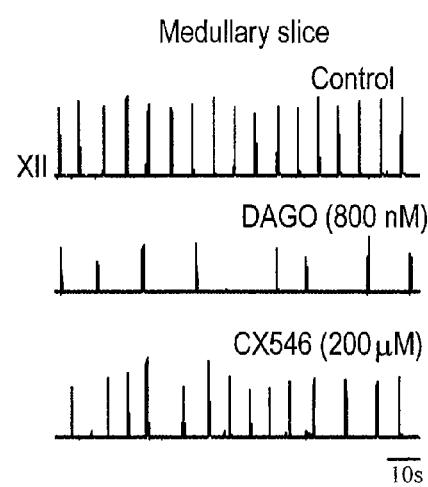
FIG. 3 shows that CX546 counters opioid-induced respiratory depression in vitro.
FIG. 3C and FIG. 3D denote population data for brainstem-spinal cord and medullary slice preparations (P1-P2 rats; n=7 for each preparation) showing the effects of bath-applied DAGO alone and then CX546 (in the continued presence of DAGO) on inspiratory frequency and burst amplitude relative to control values (of 1.0). *indicates significant difference relative to control; # indicates significant difference between value in DAGO alone and after subsequent application of CX546.
Figure 3C:
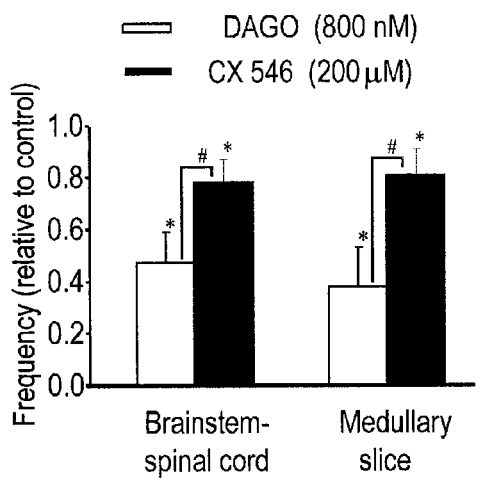
Figure 3D:
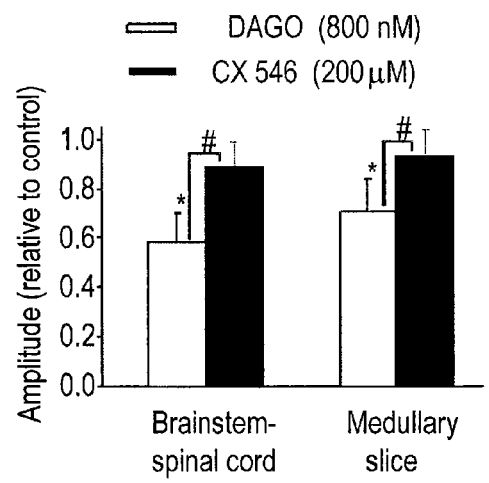

C. CX546 Alleviates DAMGO-Induced Respiratory Depression in Brainstem-Spinal Cord Preparations and in Medullary Slice Preparations The next series of experiments examined the ability of positive allosteric AMPA receptor modulator compounds CX546, CX614 and 4-(benzofurazan-5-ylcarbonyl)morpholine to counter the depression of respiratory frequency and amplitude caused by the µ-opioid receptor agonist DAMGO. FIG. 3A & FIG. 3B show recordings of rhythmic respiratory discharge generated by P1 brainstem-spinal cord and medullary slice (bathed in 9 mM [$K^+$]$_o$) preparations. DAMGO (800 nM) markedly suppressed respiratory frequency and amplitude in both preparations. The DAMGO-induced depression was alleviated by the subsequent administration of CX546 (200 µM). Population data are provided in FIGS. 3C&D. The administration of CX546 on its own did not significantly alter the control values of respiratory frequency or amplitude of motor nerve discharge generated by medullary slice preparations bathed in 9 mM [$K^+$]$_o$. Similar results were obtained following focal injection of CX614 (200 µM) or 4-(BENZOFURAZAN-5-YLCARBONYL)MORPHOLINE (1 mM) into the Pre-BötC (FIG. 6) or XII motomeuron nucleus (FIG. 7) alleviates DAMGO induced suppression of respiratory rhythm in newborn rat medullary slice preparations.

D. Perfused Heart in Situ Model

Figure 4A:
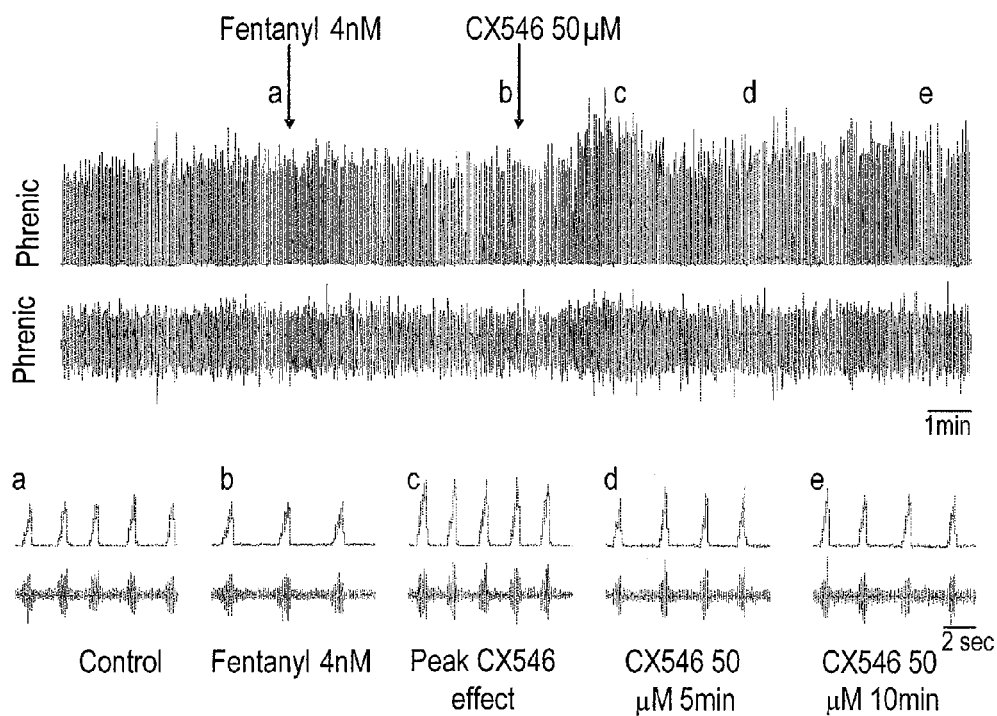
FIG. 4A denotes long-term recording of raw and integrated phrenic nerve discharge in a P24 rat. Time points at which fentanyl and CX546 were added to the reservoir containing oxygenated perfusion medium are indicated by arrows. Bottom panels show expanded sections of phrenic nerve respiratory discharge taken from the regions labelled a-e in the long-term recording.
Figure 4B:
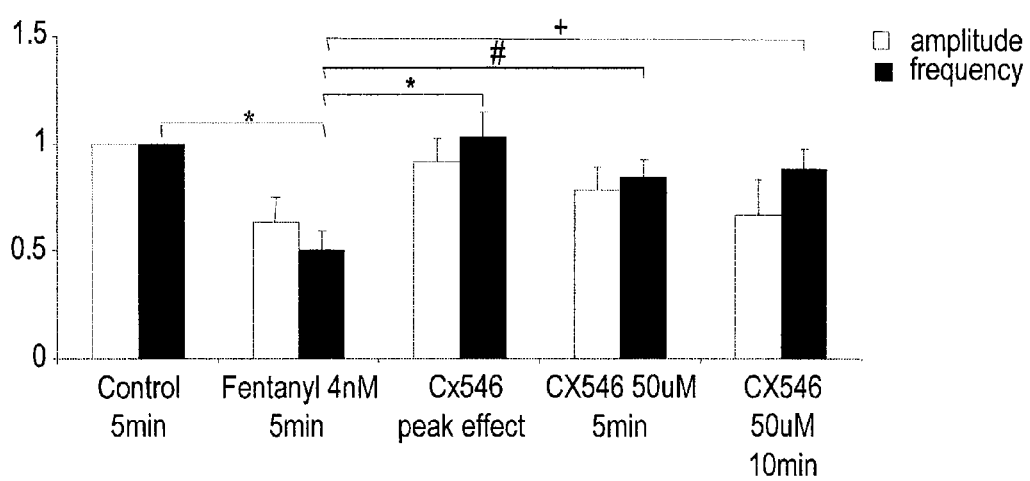
FIG. 4B denotes population data (n=8) showing the relative effects of fentanyl and CX546 (in the continued presence of fentanyl) on amplitude and frequency of integrated phrenic nerve discharge. $*p<0.001$; $\#p<0.05$; $+p<0.01$.

Rhythmically-active, brainstem-spinal cord, and medullary slice preparations in rat are not viable beyond the newborn period. However, one can examine central respiratory control and its pharmacology in reduced preparations of older rodents using the in situ working heart-brainstem preparation (see, Paton, J. F. (1996)). These preparations generate a normal (in vivo-like) breathing motor pattern which includes augmenting phrenic bursts. They are also oxygenated throughout and have uniform brain tissue pH. See, Wilson, R. J., et al. (2001) *Am. J Physiol. Regul. Integr. Comp. Physiol.* 281:R528-538. FIG. 4A shows a representative example of phrenic nerve discharge recorded from a P24 rat in situ preparation. Administration of fentanyl (4 nM) to the perfusate produced a significant decrease of respiratory frequency and phrenic burst amplitude that was countered by subsequent administration of CX546 (50 µM). Population data are presented in FIG. 4B. Detailed methods of the model are provided elsewhere, and are only briefly detailed here. See, Paton, J. F., (1996) *J. Neurosci. Meth.* 65:63-68; Day, T. A., et al. (2003) *Auton. Neurosci.* 106:50. In brief, juvenile SD rats (between 3 and 4 weeks of age, 80-120 g) were anesthetized with isoflurane, submerged in ice-cold oxygenated perfusate, decerebrated, and transected caudal to the diaphragm and the descending aorta cannulated (<8 min). The torso and brainstem were then transferred to a recording chamber where the descending aorta was cannulated with a double-lumen cannula (one line to deliver perfusate, the second to monitor blood pressure) and perfused with saline (bubbled with 95% $O_2$/5% $CO_2$) at a flow rate sufficient to generate and maintain arterial pressure at 60 mmHg. Once perfusion was initiated and arterial pressure stabilized, the animal was gradually warmed to 32° C. by heating the perfusate. The preparation was then allowed to stabilize for one hour (from the start of the dissection), during which time the left phrenic nerve was dissected for monitoring inspiratory activity (frequency and burst amplitude). After the one hour stabilization period, baseline respiratory output was recorded and the various drugs (e.g., fentanyl and CX546) added directly to the perfusate. Respiratory rhythm in perfused, in situ preparations was monitored from the phrenic nerve which was placed over two platinum hook electrodes. Signals were amplified, rectified, low-passed filtered and recorded to a computer using an analog-digital converter (Digidata 1200, Molecular Devices, Union City, Calif.) and data acquisition software (Axoscope, Molecular Devices).

Example 2

In Vivo Animal Models

The in vivo experiments described below from newborn and adult rats demonstrated that the actions of Positive allosteric AMPA receptor modulators observed in vitro and in situ also occur in the intact animal.

A. Plethysmographic Measurements

This example examined the breathing patterns generated by unanesthetized newborn (P0-P2) and adult rats. Whole-body plethysmographic measurements of the frequency and depth of breathing were made from unrestrained SD rats of either sex. Pressure changes associated with breathing were measured using either a 27 ml chamber for postnatal (P)0-P1 rats or a 2200 ml chamber for adult rats (150-200 gm), a pressure transducer (model DP 103, Validyne, Northridge, Calif.) and signal conditioner (CD-15, Validyne). For newborns, the plethysmograph was contained within an infant incubator (model C-86, Isolette, Warminster, Pa.) in order to maintain the ambient temperature at the approximate nest temperature of 32° C. See, Abel, R. A., et al. (1998) *Dev. Psychobiol.* 32(2):91-99.

Respiration was depressed by i.p. administration of either the µ-opioid receptor agonist fentanyl or the barbiturate phenobarbital. CX546 was administered intraperitoneally (i.p.) at a dosage of 16 mg/kg (dose based on Lauterborn, et al. (2000)). Fentanyl HCl (60 µg/kg for newborn and 130 µg/kg for adult rats) and phenobarbital (28 mg/kg for newborn and 100 mg/kg for adult rats) were dissolved in physiological saline and administered i.p. (5-10 µl total volume for newborn and 150-300 µl for adult rats) to reduce baseline respiratory frequency by ~50%. Administration of vehicle did not affect the respiratory parameters studied in any preparation.

Figure 5A:
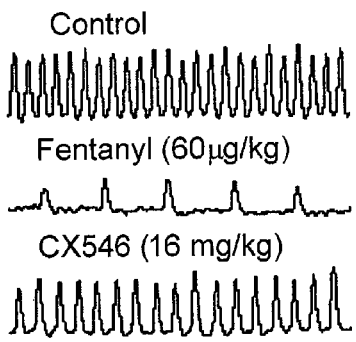
FIG. 5 shows CX546 counters opioid- and phenobarbital-induced respiratory depression in vivo. Plethysmographic recording showing that the inhibitory effect of fentanyl (FIG. 5A) and phenobarbital (FIG. 5B) on the breathing frequency and amplitude in unanesthetized P0 pups is countered by CX546.
FIG. 5C denotes plethysmographic recording from an adult rat showing that, as seen in P0 pups, administration of fentanyl inhibits breathing frequency and amplitude and that this inhibition is reduced by CX546.
FIG. 5D and FIG. 5E denote population data for P0 rat pups showing changes in frequency and amplitude relative to control evoked by fentanyl or phenobarbital both before and after the administration of CX546 (n=4).
FIG. 5F denotes population data for adult rats showing relative changes in frequency and amplitude evoked by fentanyl alone and after the administration of CX546 (n=4). *indicates significant difference relative to control; #indicates significant difference between groups indicates significant difference between values in the presence of the respiratory depressant alone and after subsequent application of CX546.
Figure 5B:
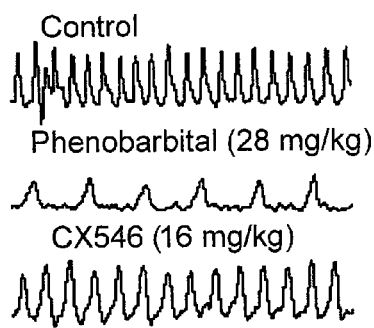
Figure 5C:
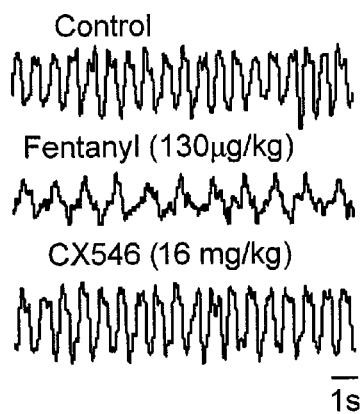
Figure 5D:
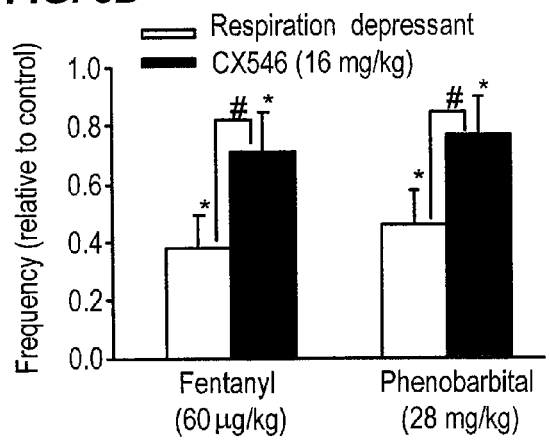
Figure 5E:
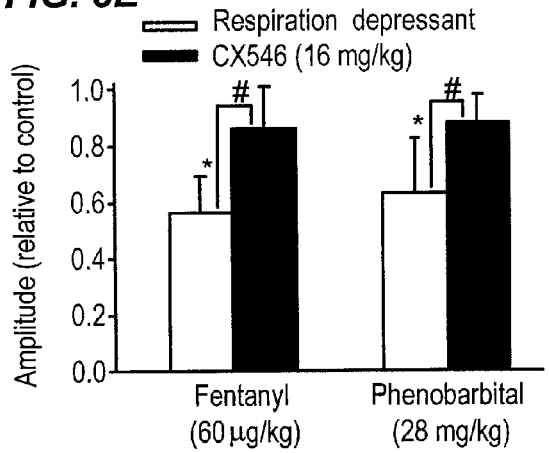
Figure 5F:
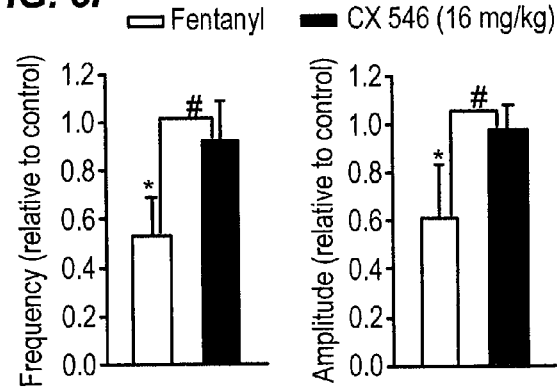
Figure 8:
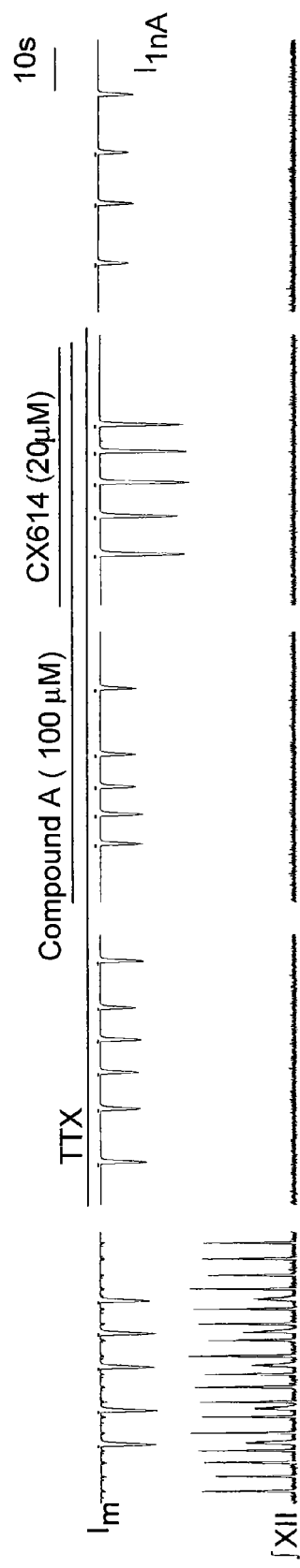
FIG. 8 shows bath-application of positive allosteric AMPA receptor modulator compounds CX614 and 4-(benzofurazan-5-ylcarbonyl)morpholine (Compound A) causes an increase in currents induced by local application of glutamate into the XII motorneuron nucleus. Voltage-clamp recordings from a XII motorneuron (top trace) and suction electrode recording of XII nerve root (bottom trace) in a rat medullary slice preparation. Left to right panels as follows: i) local injection of glutamate into the XII nucleus in a rhythmically active slice induces burst of XII nerve discharge between inspiratory bursts; ii) inward currents induced by glutamate after the addition of tetrodotoxin (TTX) to the bathing medium inhibits bursting and synaptic transmission; iii) the amplitude and duration of glutamate-induced inward currents was not significantly altered by the addition of Compound A to the bathing medium; iv) the amplitude of glutamate-induced inward currents were increased ~2-fold by the addition of CX614 to the bathing medium; v) washout of Compound A and CX614 (note that TTX is difficult to wash out, thus the lack of re-emergence of the respiratory rhythm).
Figure 9:
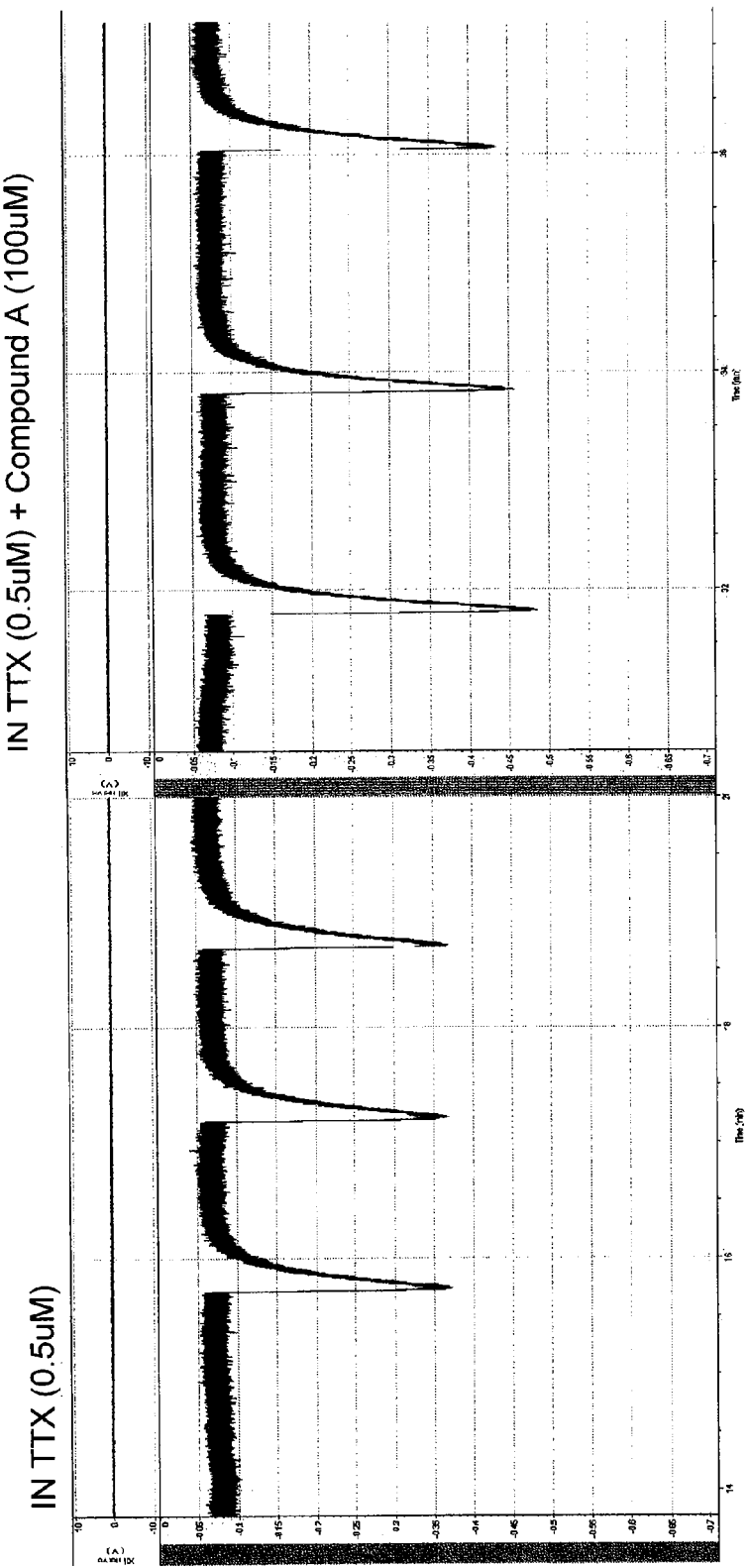
FIG. 9 shows bath application of 4-(benzofurazan-5-ylcarbonyl)morpholine (Compound A) causes an increase in currents induced by local application of glutamate into the preBötzinger complex. Data shows a voltage-clamp recording from an inspiratory neuron within the preBötzinger complex of a rat medullary slice preparation. Left panel shows inward currents in response to local glutamate application in the presence of TTX-to prevent indirect effects via synaptic inputs. Right panel shows that the current amplitude in response to glutamate injections increases in the presence of Compound A.
Figure 10:
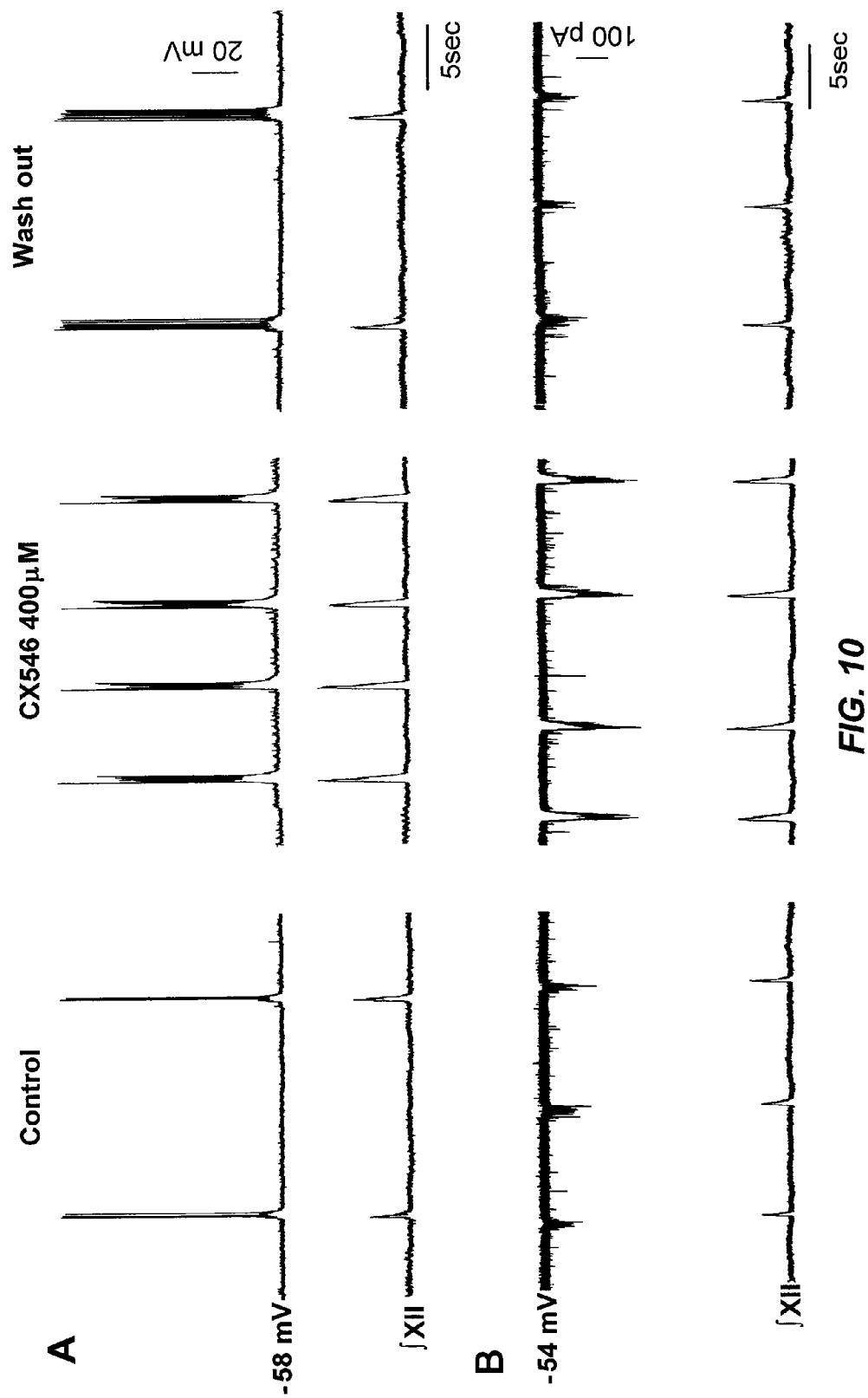
FIG. 10 shows whole-cell analyses of CX546 effects on an inspiratory neuron within the preBötC.

Inter-breath intervals and the relative amplitude of volume excursions associated with each breath were calculated before and after (5 minutes) i.p. drug administration. In all cases, values are given as means and standard deviations. Statistical significance was tested using Student's t test for paired or unpaired data (two groups) or one way repeated measures ANOVA (multiple groups) followed by Holm-sidak test for multiple comparisons. Significance was accepted at p values lower than 0.05. As shown in representative examples in FIGS. 5A, 5B and 5C and in the population data of FIGS. 5D, 5E and 5F, both of the µ-opioid receptor agonist significantly decreased respiratory frequency and burst amplitude. Subsequent i.p. injection of CX546 (16 mg/kg) reversed the opiate- and phenobarbital-mediated respiratory depression. The baseline frequency and amplitude of newborn (P0-P2, n=5) and adult rats (n=3, data not shown), however, were not significantly altered by the same dose of CX546 on its own. CX546 was also without any obvious effect on the behaviour or of arousal-state (i.e. increase/decrease in spontaneous movement, agitation, indication of sedation) of the rats.

B. Nociceptive Testing

To determine whether the i.p. administration of CX546 affects fentanyl-induced analgesia in vivo, a thermal nociception test was used. Thermal nociception was measured by a modification of a previously reported method. See, Hargreaves, K., et al., (1988) *Pain* 32:77-88. Briefly, unrestrained rats were placed in a plastic chamber (14×16×22 cm) and allowed to acclimate for 10 min. before testing. The plantar test apparatus (Ugo Basile, Comerio, VA, Italy) consisted of a movable infrared heat source (OSRAM 8V 50W halogen lamp) which was positioned directly beneath the hind paw, 20 mm below the chamber floor. Heat settings were 30 and 50 (manufacturer settings) for newborn and adult rats, respectively. The instrument detected paw withdrawal latency from the onset of heat exposure, with an accuracy to 0.1 sec. When the rat perceived pain and withdrew its paw, the instrument automatically detected the withdrawal latency to the nearest 0.1 sec.. Withdrawal latencies were recorded before, during, and after each drug administration. The heat stimulus was automatically terminated if a withdrawal response was not observed within 20 sec. of its onset.

The measured results from the thermal nociception test showed that the latency of hind paw withdrawal was 4.9±3.8 s and 5.6±1.7 s for newborns and adult rats, respectively (see Table 1). Administration of the fentanyl at doses that suppressed respiratory rhythm (60 µg/kg for newborn and 130 µg/kg for adult rats) extended the latency to paw-withdrawal to the 20 sec cut-off limit. Thus, fentanyl-induced analgesia, which manifest in the loss of foot withdrawal, persisted despite the subsequent i.p. administration of CX546 (16 mg/kg). The fentanyl-induced analgesic effect, was however, blocked by the subsequent administration of naloxone (1 mg/kg) in both newborn and adult rats. When CX546 (16 mg/kg) was administered on its own, it did not change the sensitivity of thermal nociception tests in the control condition. These results demonstrate that CX546 reduces the deleterious respiratory-depressant effects of opioids without inhibiting their desirable, analgesic actions.

TABLE 1

Drug effects on thermal nociception using hind paw withdrawal tests

| | Newborn (P1-P2) | | Adult (2-3 months) | |
|---|---|---|---|---|
| | Latency (s) | n | Latency (s) | n |
| Control | 4.9 ± 3.8 | 7 | 5.6 ± 1.7 | 6 |
| CX546 pre-administration of fentanyl | 4.3 ± 3.2 | 4 | 5.3 ± 2.1 | 4 |
| Fentanyl | >20* | 5 | >20* | 4 |
| CX546 post-administration of fentanyl | >20* | 5 | >20* | 4 |
| Naloxone post-administration of fentanyl | 4.0 ± 3.1 | 4 | 4.8 ± 1.9 | 3 |

Administration of CX546 (16 mg/kg) was tested pre- and post-administration of fentanyl (60 µg/kg for newborn and 130 µg/kg for adult rats). Naloxone dose was 1 mg/kg. All drugs were administrated i.p.
*indicates significant difference relative to control (p values < 0.05).

Figure 11:
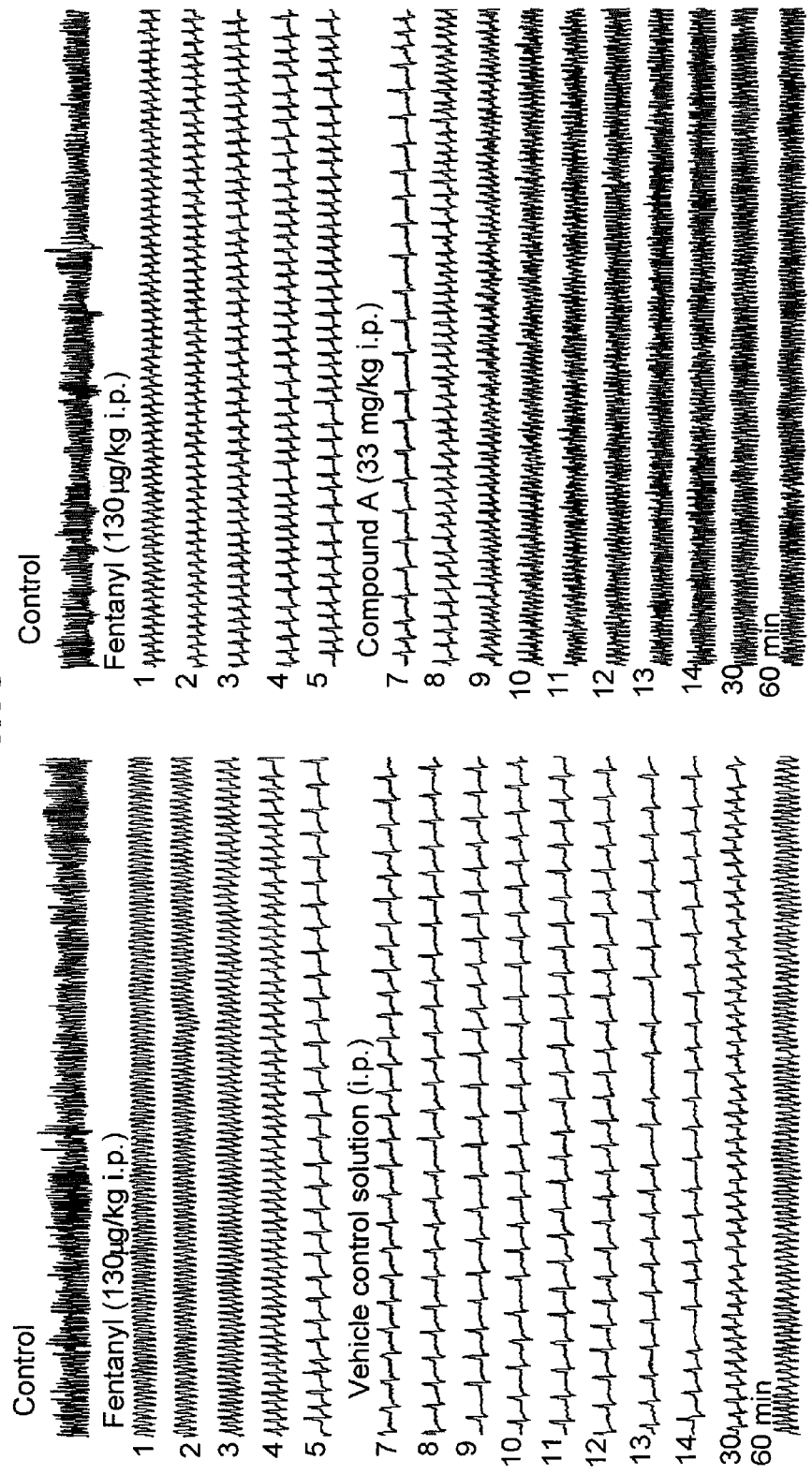
FIG. 11 shows whole-body plethysmographic measurements of the frequency and depth of breathing from unrestrained Sprague-Dawley rat. Respiration was depressed by intraperitoneal (i.p.) administration of the μ-opioid receptor agonist fentanyl (130 μg/kg) denoted by the significantly decreased respiratory frequency and amplitude within a few minutes of administration (numbers on the left of traces refer to minutes after fentanyl injection). The respiratory depression was still evident at 1 hour. Left trace shows the subsequent i.p. injection of the vehicle, hydroxypropyl-beta-cyclodextrin (HPCD), solution without 4-(benzofurazan-5-ylcarbonyl)morpholine (Compound A) had no effects on the opiate-mediated suppression of respiratory rhythm. The right trace shows another P17 rat, treated with fentanyl as described above, but given a subsequent i.p. injection of Compound A) (33 mg/kg, made with HPCD solution) reversed the fentanyl-induced respiratory depression within five-minutes. The enhancement of the respiratory rhythm by Compound A persisted for at least 1 hour. Compound A did not result in any obvious effect on the behaviour or arousal state of the animal (i.e., increase/decrease in spontaneous movement, agitation, indication of sedation).
Figure 12:
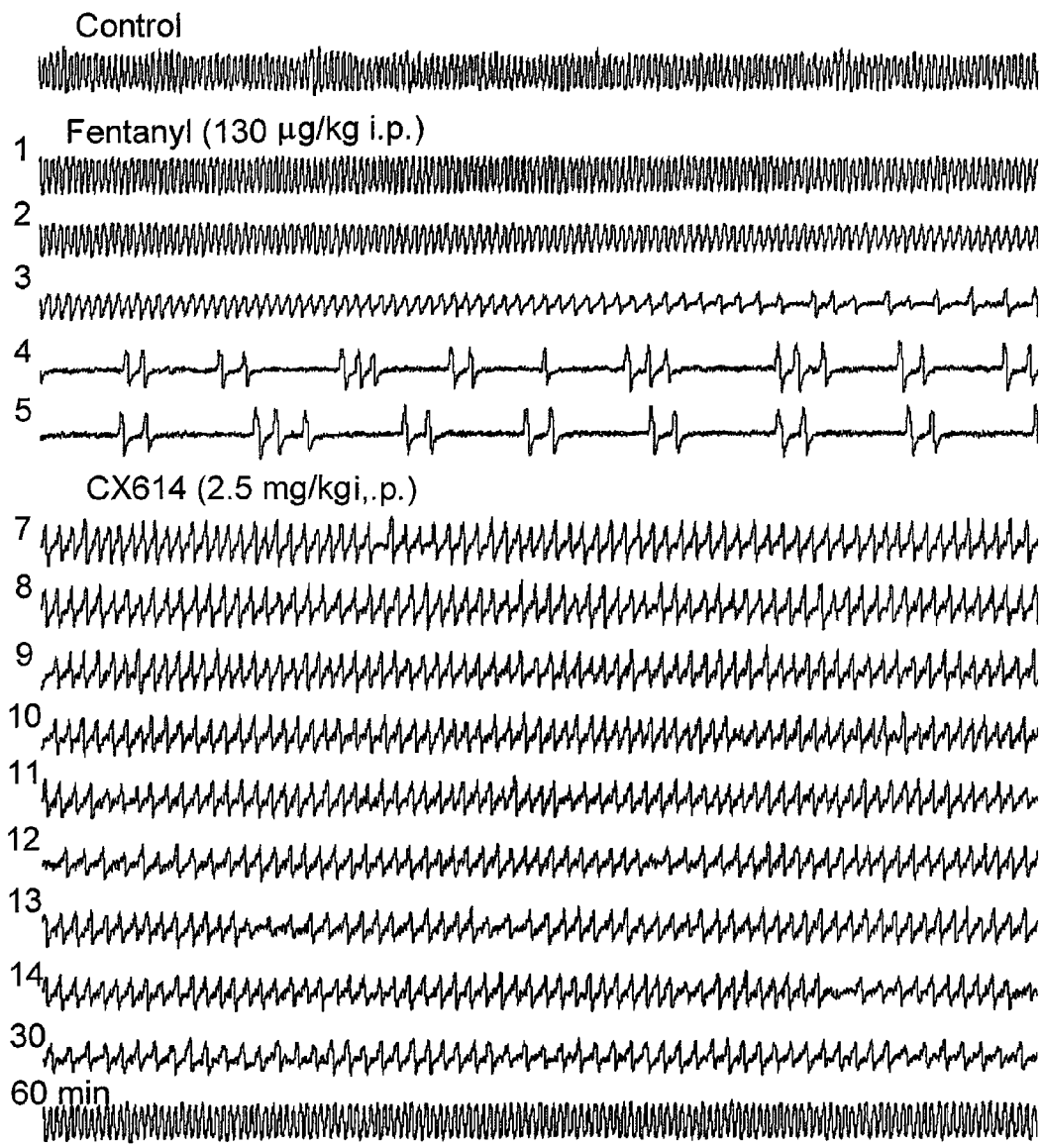
FIG. 12 shows whole-body plethysmographic measurements of the frequency and depth of breathing from unrestrained Sprague-Dawley rat. Respiration was depressed by intraperitoneal (i.p.) administration of the p-opioid receptor agonist fentanyl (130 μg/kg) denoted by the significantly decreased respiratory frequency and amplitude within a few minutes of administration (numbers on the left of traces refer to minutes after fentanyl injection). Subsequent injection of CX614 (2.5 mg/kg, made with HPCD solution) reversed the fentanyl-induced respiratory depression. The enhancement of respiratory rhythm by CX614 persisted for at least 1 hour. CX614 was also without any obvious effect on the behaviour or arousal state (i.e., increase/decrease in spontaneous movement, agitation, indication of sedation) of the rats.

C. Effects of Positive Allosteric AMPA Receptor Modulator Compounds CX614 and 4-(Benzofurazan-5-Ylcarbonyl)Morpholine in Vivo for Alleviating Opiate-Induced Respiratory Depression To demonstrate that the effects of positive allosteric AMPA receptor modulators as seen in the above experiments were not unique to CX546, the actions of CX614 and 4-(benzofurazan-5-ylcarbonyl)morpholine on opiate-induced respiratory depression were examined in SD rats in vivo with whole body plethysmography. Whole-body plethysmographic measurements of the frequency and depth of breathing were made from unrestrained SD rats. Pressure changes associated with breathing were measured with a 300-ml chamber for P17 rats (~35 g), a pressure transducer (model DP 103; Validyne Engineering, Northridge, Calif.), and a signal conditioner (CD-15; Validyne Engineering). Respiration was depressed by i.p. administration of the µ-opioid receptor agonist fentanyl (130 µg/kg). As shown in FIGS. 11 and 12, fentanyl significantly decreased respiratory frequency and amplitude within a few minutes of administration (numbers on the left of traces refer to minutes after fentanyl injection). The respiratory depression was still evident at 1 hour. The subsequent i.p. injection of the vehicle HPCD solution without a positive allosteric AMPA receptor modulator compound had no effect on the opiate-mediated suppression of respiratory rhythm (see, FIG. 11, right trace). It is notable that the time course of fentanyl-induced depression of breathing with vehicle injection is the same as previously observed in experiments without any intervention.

In another P17 rat, the subsequent injection of 4-(benzofurazan-5-ylcarbonyl)morpholine (33 mg/kg, made with HPCD solution) reversed the fentanyl-induced respiratory depression within 5 min (see, FIG. 11, left trace). The enhancement of respiratory rhythm by 4-(benzofurazan-5-ylcarbonyl)morpholine persisted for at least 1 hour. 4-(benzofurazan-5-ylcarbonyl)morpholine was also without any obvious effect on the behaviour or arousal state (i.e., increase/decrease in spontaneous movement, agitation, indication of sedation) of the rats. In a separate experiment, fentanyl-induced respiratory depression was partially alleviated with doses as low as 20 mg/kg of 4-(benzofurazan-5-ylcarbonyl) morpholine.

In another P17 rat, the subsequent injection of CX614 (2.5 mg/kg made with HPCD solution) also reversed the fentanyl-induced respiratory depression within minutes (see, FIG. 12). The enhancement of the respiratory rhythm persisted for at least 1 hour, as with the administration of 4-(benzofurazan-5-ylcarbonyl)morpholine. CX614 was also without any obvious effect on the behaviour or arousal state (i.e., increase/decrease in spontaneous movement, agitation, indication of sedation) of the rats.

Example 3

Treatment of a Patient Having Respiratory Depression with a Positive Allosteric AMPA Receptor Modulator This example details the treatment of a patient having respiratory depression with a positive allosteric AMPA receptor modulator. The first step in the treatment process is diagnosis of respiratory depression by a skilled artisan. This can be accomplished by visual inspection of the patient having a bluish tint to the skin, and the noticeable absence of breathing or hypoventilation as evidenced by shallow infrequent breaths.

A positive allosteric AMPA receptor modulator (e.g. CX614) prepared in a sterile buffered physiological saline solution can be administered to the patient via intravenous injection at a dosage of about 0.1 to 10 mg CX614/kg body weight.

The patient is then monitored for changes in respiration, using the criteria set forth above, including skin hue, and/or depth and frequency of breaths. Additional positive allosteric AMPA receptor modulator can be delivered until the patient's breathing has stabilized to normal levels.

What is claimed is:

1. A method for reducing or inhibiting respiratory depression in a subject, comprising administering to the subject having respiratory depression a therapeutically effective amount of a positive allosteric AMPA receptor modulator sufficient to reduce or inhibit the respiratory depression.

2. The method of claim 1, wherein the respiratory depression results from treatment with an alcohol, an opiate, an opioid, or a barbiturate.

3. The method of claim 1, wherein the respiratory depression results from a drug overdose.

4. The method of claim 1, wherein the respiratory depression results from the use of a central respiratory depressant.

5. A method for inducing analgesia, anaesthesia or sedation in a subject, while simultaneously reducing or inhibiting respiratory depression in the subject, comprising administering to the subject a therapeutically effective amount of a central respiratory depressant, sufficient to induce analgesia, anaesthesia or sedation in the subject; and concomitantly administering a therapeutically effective amount of a positive allosteric AMPA receptor modulator, sufficient to reduce or inhibit respiratory depression resulting from the central respiratory depressant.

6. The method of claim 5, wherein the central respiratory depressant is selected from the group consisting of: an alcohol, an opiate, an opioid, and a barbiturate.

7. The method of claim 1 or 5, wherein the positive allosteric AMPA receptor modulator is selected from the group consisting of: CX546, CX614, 1-(benzofurazan-5-ylcarbonyl)-4,4-difluoropiperidine, and 4-(benzofurazan-5-ylcarbonyl)morpholine.

8. The method of claim 1 or 5 wherein the subject is a mammal.

9. The method of claim 8, wherein the mammal is a human.

10. The method of claim 8, wherein the mammal is selected from the group consisting of: non-human primates, kine, horses, pigs, goats, sheep, dogs, cats, rabbits, mice and rats.

11. A pharmaceutical composition for inducing analgesia, anesthesia or sedation in a subject, while simultaneously reducing or inhibiting respiratory depression in the subject, comprising, in combination, a central respiratory depressant, an positive allosteric AMPA receptor modulator, and a pharmaceutically suitable carrier.

* * * * *